United States Patent [19]

Nakajima et al.

[11] Patent Number: 4,906,627
[45] Date of Patent: Mar. 6, 1990

[54] PYRIDAZINONE DERIVATIVES, AND INSECTICIDAL, ACARICIDAL AND NEMATICIDAL COMPOSITIONS

[75] Inventors: Yasuyuki Nakajima; Yasuo Kawamura; Tomoyuki Ogura; Takahiro Makabe, all of Funabashi; Kiminori Hirata, Minamisaitama; Masaki Kudo, Minamisaitama; Yoshinori Ochiai, Minamisaitama; Masayoshi Hirose, Tokyo, all of Japan

[73] Assignee: Nissan Chemical Industries, Ltd., Tokyo, Japan

[21] Appl. No.: 191,260

[22] Filed: May 6, 1988

Related U.S. Application Data

[63] Continuation-in-part of Ser. No. 8,359, Jan. 29, 1987, abandoned.

[30] Foreign Application Priority Data

Feb. 8, 1986 [JP] Japan .................... 61-24978

[51] Int. Cl.⁴ ............... C07D 237/06; A01N 43/54
[52] U.S. Cl. ....................... 514/247; 544/241
[58] Field of Search ............... 544/239, 241; 514/247

[56] References Cited

U.S. PATENT DOCUMENTS

| | | | |
|---|---|---|---|
| 2,832,780 | 4/1958 | King . | |
| 3,137,696 | 6/1964 | Reicheneder et al. . | |
| 3,346,577 | 10/1967 | Nakagone et al. . | |
| 4,177,273 | 12/1979 | Bennett . | |
| 4,571,397 | 2/1986 | Taniguchi et al. | 544/239 |
| 4,576,630 | 3/1986 | Parg et al. . | |
| 4,663,324 | 5/1987 | Graf et al. . | |
| 4,783,462 | 11/1988 | Mutsukado | 544/239 |
| 4,820,704 | 4/1989 | Richarz et al. | 514/247 |
| 4,837,217 | 6/1989 | Ogura et al. | 544/241 |

FOREIGN PATENT DOCUMENTS

| | | |
|---|---|---|
| 78450 | 5/1983 | European Pat. Off. . |
| 88384 | 9/1983 | European Pat. Off. . |
| 134439 | 3/1985 | European Pat. Off. . |
| 135076 | 3/1985 | European Pat. Off. . |
| 183212 | 6/1986 | European Pat. Off. . |
| 193853 | 9/1986 | European Pat. Off. . |
| 199281 | 10/1986 | European Pat. Off. . |
| 3143303 | 5/1983 | Fed. Rep. of Germany . |
| 3328770 | 2/1985 | Fed. Rep. of Germany . |
| 225039 | 7/1985 | Fed. Rep. of Germany . |
| 38-7998 | 6/1963 | Japan . |
| 40-03798 | 2/1965 | Japan . |
| 41-2459 | 2/1966 | Japan . |
| 41-2788 | 2/1966 | Japan . |
| 42-1302 | 1/1967 | Japan . |
| 42-9344 | 5/1967 | Japan . |
| 43-11902 | 5/1968 | Japan . |
| 43-11903 | 5/1968 | Japan . |
| 43-11904 | 5/1968 | Japan . |
| 42-11905 | 5/1968 | Japan . |
| 43-11906 | 5/1968 | Japan . |
| 43-11907 | 5/1968 | Japan . |
| 43-11908 | 5/1968 | Japan . |
| 43-11909 | 5/1968 | Japan . |
| 44-8857 | 4/1969 | Japan . |
| 44-8858 | 4/1969 | Japan . |
| 44-8859 | 4/1969 | Japan . |
| 44-8860 | 4/1969 | Japan . |
| 44-8861 | 4/1969 | Japan . |
| 44-12421 | 6/1969 | Japan . |
| 61-130275 | 6/1986 | Japan . |
| 61-243078 | 10/1986 | Japan . |
| 61-268672 | 11/1986 | Japan . |

OTHER PUBLICATIONS

Japanese Patent Abstract of Laid-Open Appln JP 60-4173, May 16, 1985, vol. 9, No. 112 (c-281) (1835).
Japanese Patent Abstract of Laid-Open Appln JP 60-54319, Jul. 30, 1985, vol. 9, No. 184 (c-294) (1907).
Chemical Abstract No. 114552g, vol. 93, 1980.
Chemical Abstract No. 20533h, vol. 91, 1979.
Chemical Abstract No. 124615j, vol. 78, 1972.
Chemical Abstract No. 106726f, vol. 69, 1968.
Chemical Abstract No. 34565m, vol. 100, 1984.
Chemical Abstract No. 30484u, vol. 71, 1969.
Chemical Abstract No. 106728h, vol. 69, 1968.
Kaju, Chem. Abs. vol. 70, 1969, 28883j, Synthesis of Sulfur-Containing Pyridazines.

Primary Examiner—Donald G. Daus
Attorney, Agent, or Firm—Oliff & Berridge

[57] ABSTRACT

Compounds of the following formula:

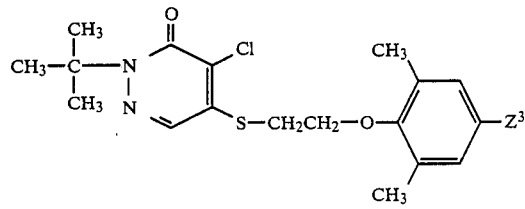

wherein $Z^3$ represents halogen atom, straight or branched chain alkyl group having 1 to 10 carbon atoms, alkoxy group having 1 to 10 carbon atoms, alkylcarbonyl having 2 to 10 carbon atoms, alkoxyalkyl group having 2 to 4 carbon atoms,

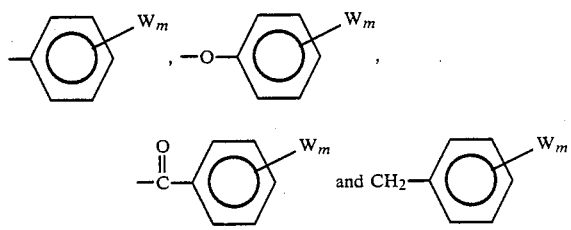

W represents halogen atom, alkyl group having 1 to 4 carbon atoms, alkoxy group having 1 to 4 carbon atoms, haloalkyl group having 1 to 4 carbon atoms, or nitro group, m is 0 or an integer of 1 to 2, and when m is 2, W may be same or different, and compositions for controlling insects, acari and nemati which contain such compound.

7 Claims, No Drawings

PYRIDAZINONE DERIVATIVES, AND INSECTICIDAL, ACARICIDAL AND NEMATICIDAL COMPOSITIONS

This is a continuation-in-part application of Ser. No. 008,359 filed Jan. 29, 1987 (now abandoned).

BACKGROUND OF THE INVENTION

1. Field of the Invention

This invention relates to novel 3(2H)-pyridazinone derivatives; preparation thereof; insecticidal, acaricidal, and nematicidal compositions for agricultural and horticultural uses; and expellent compositions for ticks parasitic on animals; said compositions containing said derivatives as an active ingredient.

2. Description of the Prior Art

The present invention concerns EP-A-0088384, EP-A-0134439, EP-A-0183212 and EP-A-0199281. The known compounds contained in these patent applications are represented by the general formula (IV):

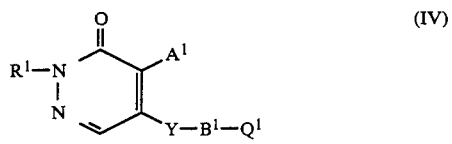

The characteristics of the compounds of these patent applications are, e.g., in the formula (IV):

in case of EP-A-0088384 and EP-A-0134439, Y represents oxygen atom or sulfur atom, but benzyl derivative group is bound thereto as -B'-Q';

in case of EP-A-0183212, A' represents alkyl group or it has double bond or triple bond as B';

in case of EP-A-0199281, Q' represents heterocyclic ring or specific substituent.

The present inventors have intensively conducted research on pyridazinone derivatives which are different from these EPC patent applications in chemical structure and have obtained the present compounds of the general formula (I) given below.

Furthermore, the present inventors have found out that the present compounds of the general formula (I) given below have excellent effective insecticidal, acaricidal and nematicidal activities.

For example, the group of known compounds represented by the aforesaid general formula (IV) have strong insecticidal, acaricidal and nematicidal activities. Even in comparison with those known compounds, however, the present compounds exhibited remarkable activity rise in respect to residual activity, especially for insecticidal and acaricidal activity. Therefore, the present invention was completed by finding out that the present compounds can effectively control pests which are agriculturally and horticulturally harmful even with an extremely low drug concentration in comparison with the known compounds represented by the general formula (IV).

SUMMARY OF THE INVENTION

An object of this invention is to provide novel 3(2H)-pyridazinone derivatives which have insecticidal, acaricidal and nematicidal activities.

Another object of this invention is to provide a process for preparing such 3(2H)-pyridazinone derivatives.

Further object of this invention is to provide insecticidal, acaricidal and nematicidal compositions containing 3(2H)-pyridazinone derivatives as an active ingredient.

Still further object of this invention is to provide a method for controlling pests by using the above-mentioned derivatives or compositions.

Other objects of this invention will become apparent from the description given below.

DETAILED DESCRIPTION OF THE INVENTION

The pyridazinone derivatives according to the invention have the general formula (I):

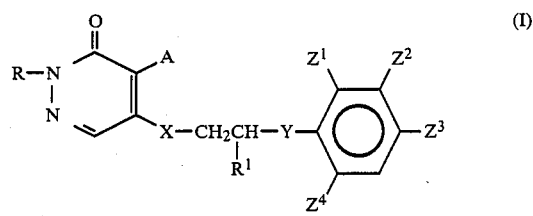

wherein

R represents a straight or branched chain alkyl group having 2 to 6 carbon atoms, A represents halogen atom, X represents oxygen atom or sulfur atom, Y represents oxygen atom, sulfur atom, or $CH_2$, $R^1$ represents hydrogen atom or alkyl having 1 to 4 carbon atoms, $Z^1$ and $Z^4$ represent independently hydrogen atom, alkyl group having 1 to 4 carbon atoms, halogen atom, alkoxy group having 1 to 4 carbon atoms or nitro group, with the proviso that when X represents oxygen atom, $Z^1$ and $Z^4$ do not represent hydrogen atom; $Z^2$ represents hydrogen atom, alkyl group having 1 to 4 carbon atoms or alkoxy group having 1 to 4 carbon atoms;

$Z^3$ represents hydrogen atom, halogen atom, straight or branched chain alkyl group having 1 to 10 carbon atoms, alkenyl group having 2 to 5 carbon atoms, cycloalkyl group having 3 to 6 carbon atoms, straight or branched chain alkoxy group having 1 to 10 carbon atoms, alkylthio group having 1 to 10 carbon atoms, alkylsulfinyl group having 1 to 10 carbon atoms, alkylsulfonyl group having 1 to 10 carbon atoms, haloalkyl group having 1 to 5 carbon atoms, haloalkyloxy group having 1 to 5 carbon atoms, alkylcarbonyl amino group having 2 to 5 carbon atoms, nitro group, alkylcarbonyl group having 1 to 10 carbon atoms, napthylcarbonyl group, $-COCH_2C_6H_5$ group, 2-phenylethyl group, hydroxyalkyl group having 1 to 4 carbon atoms, alkoxyalkyl group having 2 to 4 carbon atoms, alkylthioalkyl group having 2 to 4 carbon atoms, alkoxyiminoalkyl group having 2 to 4 carbon atoms, $-NHSO_2CH_3$ group, $-NHCON(CH_3)_2$ group,

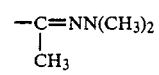

group, cycloalkylcarbonyl group having 4 to 7 carbon atoms or cycloalkylmethyl group having 4 to 7 carbon atoms,

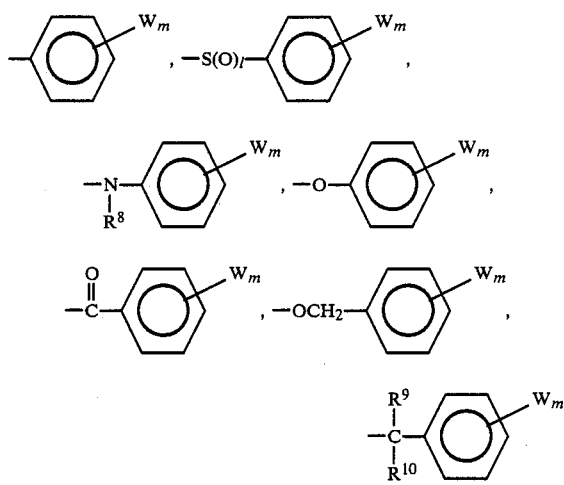

provided that l represents 0 or an integer of 1 to 2, $R^8$ represents hydrogen atom, alkyl group having 1 to 4 carbon atoms or alkylcarbonyl group having 1 to 4 carbon atoms, $R^9$ to $R^{10}$ represent independently hydrogen atom, alkyl group having 1 to 4 carbon atoms, halogen atom, or alkoxy group having 1 to 4 carbon atoms, W represents halogen atom, alkyl group having 1 to 4 carbon atoms, alkoxy group having 1 to 4 carbon atoms, haloalkyl group having 1 to 4 carbon atoms, or nitro group, m is 0 or an integer of 1 to 2, and when m is 2, W may be same or different, with the proviso that $Z^1$, $Z^2$, $Z^3$ and $Z^4$ do not simultaneously represent hydrogen atom.

In respect to the activity for controlling pests, preferable compounds of the present invention are ones in which, in the general formula (I), R represents t-Bu, A represents chlorine atom, $R^1$ represents hydrogen atom, and Y represents oxygen atom.

More preferred compounds of the general formula (I) among the compounds shown in Tables 1 to 3 are:

| Nos. | 36, 38, 40, 46, 49, 55, 71, 72, 73, 74, 84, 85, 88, 89, 90, 92, 111, 112, 113, 127, 128, 129, 426, 427, 429, 430, 432, 438, 443, 463, 465, 466, 468, 470, 472, 474, 476, 477, 480, 481, 482, 484, 488, 490, 491, 492, 494, 496, 514, 517, 518, 520, 522, 524, 528, 540, 542, 850, 851, 852, 857, 863 and 895. |
|---|---|

The compounds shown in Tables 1, 2 and 3 are examples. However, the present invention is not restricted to these compounds which are shown as only exemplification.

In Tables 1, 2 and 3, t, i, c and s mean tertiary, iso, cyclo and secondary, respectively, and each symbol Me, Et, Pr, Bu, Am, Pen, Hex and Ph means methyl, ethyl, propyl, butyl, amyl, pentyl, hexyl and phenyl, respectively.

In case of the compounds containing asymmetric carbon atoms among the compounds covered by the present invention, optical isomers, i.e., (+)-isomers and (−)-isomers are also included in the present invention.

TABLE 1

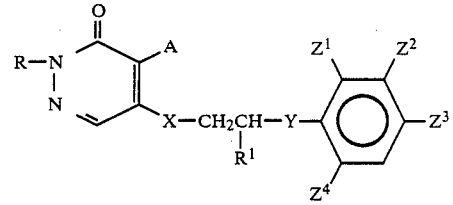

| No. | R | A | X | $R^1$ | Y | $Z^1$ | $Z^2$ | $Z^3$ | $Z^4$ |
|---|---|---|---|---|---|---|---|---|---|
| 12 | t-Bu | Cl | S | H | O | Me | H | H | H |
| 13 | t-Bu | Cl | S | H | O | H | H | Et | H |
| 14 | t-Bu | Cl | S | H | O | H | H | Pr | H |
| 15 | t-Bu | Cl | S | H | O | i-Pr | H | H | H |
| 16 | t-Bu | Cl | S | H | O | H | H | Bu | H |
| 17 | t-Bu | Cl | S | H | O | H | H | Pen | H |
| 18 | t-Bu | Cl | S | H | O | H | OPr | H | H |
| 19 | t-Bu | Cl | S | H | O | H | H | OBu | H |
| 20 | t-Bu | Cl | S | H | O | H | H | SMe | H |
| 21 | t-Bu | Cl | S | H | O | Me | H | Cl | H |
| 22 | t-Bu | Cl | S | H | O | Me | H | Me | H |
| 23 | t-Bu | Cl | S | H | O | H | Me | H | Me |
| 24 | t-Bu | Cl | S | H | O | Me | H | H | Me |
| 25 | t-Bu | Cl | S | H | O | Me | H | Pen | H |
| 26 | t-Bu | Cl | S | H | O | Et | H | Pen | H |
| 27 | t-Bu | Cl | S | H | O | Me | H | CO(CH$_2$)$_3$CH$_3$ | H |
| 28 | t-Bu | Cl | S | H | O | OMe | H | H | OMe |
| 29 | t-Bu | Cl | S | H | O | Me | H | H | Cl |
| 30 | t-Bu | Cl | S | H | O | Cl | H | H | Cl |
| 31 | t-Bu | Cl | S | H | O | Me | H | Cl | Cl |
| 32 | t-Bu | Cl | S | H | O | Me | Me | H | Me |
| 33 | t-Bu | Cl | S | H | O | Me | H | Me | Me |
| 34 | t-Bu | Cl | S | H | O | Me | H | Br | Cl |
| 35 | t-Bu | Cl | S | H | O | Me | H | COCH$_2$CH$_3$ | Cl |
| 36 | t-Bu | Cl | S | H | O | Me | H | Pr | Cl |
| 37 | t-Bu | Cl | S | H | O | Me | H | Bu | Cl |
| 38 | t-Bu | Cl | S | H | O | Cl | H | COCH$_2$CH$_3$ | Cl |

TABLE 1-continued

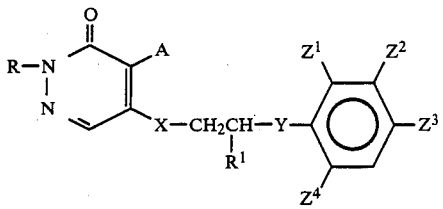

| No. | R | A | X | R¹ | Y | Z¹ | Z² | Z³ | Z⁴ |
|---|---|---|---|---|---|---|---|---|---|
| 39 | t-Bu | Cl | S | H | O | Cl | H | Et | Cl |
| 40 | t-Bu | Cl | S | H | O | Cl | H | Pr | Cl |
| 41 | t-Bu | Cl | S | H | O | Cl | H | i-Pr | Cl |
| 42 | t-Bu | Cl | S | H | O | Cl | H | Bu | Cl |
| 43 | t-Bu | Cl | S | H | O | Cl | H | i-Bu | Cl |
| 44 | t-Bu | Cl | S | H | O | Cl | H | t-Bu | Cl |
| 45 | t-Bu | Cl | S | H | O | Cl | H | Pen | Cl |
| 46 | t-Bu | Cl | S | H | O | Cl | H | Ph | Cl |
| 47 | t-Bu | Cl | S | H | O | Br | H | $COCH_2CH_3$ | Br |
| 48 | t-Bu | Cl | S | H | O | Br | H | Et | Br |
| 49 | t-Bu | Cl | S | H | O | Br | H | Pr | Br |
| 50 | t-Bu | Cl | S | H | O | Br | H | i-Pr | Br |
| 51 | t-Bu | Cl | S | H | O | Br | H | Bu | Br |
| 52 | t-Bu | Cl | S | H | O | Br | H | i-Bu | Br |
| 53 | t-Bu | Cl | S | H | O | Br | H | t-Bu | Br |
| 54 | t-Bu | Cl | S | H | O | Br | H | Ph | Br |
| 55 | t-Bu | Cl | S | H | O | F | H | $COCH_2CH_3$ | F |
| 56 | t-Bu | Cl | S | H | O | F | H | $CH=CHCH_3$ | F |
| 57 | t-Bu | Cl | S | H | O | F | H | Pr | F |
| 58 | t-Bu | Cl | S | H | O | F | H | Bu | F |
| 59 | t-Bu | Cl | S | H | O | F | H | Pen | F |
| 60 | t-Bu | Cl | S | H | O | F | H | Et | F |
| 61 | t-Bu | Cl | S | H | O | $NO_2$ | H | Me | $NO_2$ |
| 62 | t-Bu | Cl | S | H | O | $NO_2$ | H | Et | $NO_2$ |
| 63 | t-Bu | Cl | S | H | O | $NO_2$ | H | Pr | $NO_2$ |
| 64 | t-Bu | Cl | S | H | O | $NO_2$ | H | Bu | $NO_2$ |
| 65 | t-Bu | Cl | S | H | O | $NO_2$ | H | Pen | $NO_2$ |
| 66 | t-Bu | Cl | S | H | O | OMe | H | Et | OMe |
| 67 | t-Bu | Cl | S | H | O | OMe | H | Pr | OMe |
| 68 | t-Bu | Cl | S | H | O | OMe | H | i-Pr | OMe |
| 69 | t-Bu | Cl | S | H | O | OMe | H | Bu | OMe |
| 70 | t-Bu | Cl | S | H | O | OMe | H | t-Bu | OMe |
| 71 | t-Bu | Cl | S | H | O | Me | H | $COCH_3$ | Me |
| 72 | t-Bu | Cl | S | H | O | Me | H | $COCH_2CH_3$ | Me |
| 73 | t-Bu | Cl | S | H | O | Me | H | $COCH_2CH_2CH_3$ | Me |
| 74 | t-Bu | Cl | S | H | O | Me | H | $COCH(CH_3)_2$ | Me |
| 75 | t-Bu | Cl | S | H | O | Me | H | CO—c-Pr | Me |
| 76 | t-Bu | Cl | S | H | O | Me | H | $CO(CH_2)_3CH_3$ | Me |
| 77 | t-Bu | Cl | S | H | O | Me | H | CO—c-Hex | Me |
| 78 | t-Bu | Cl | S | H | O | Me | H | $CO(CH_2)_4CH_3$ | Me |
| 79 | t-Bu | Cl | S | H | O | Me | H | $CO(CH_2)_6CH_3$ | Me |
| 80 | t-Bu | Cl | S | H | O | Me | H | $CO(CH_2)_8CH_3$ | Me |
| 81 | t-Bu | Cl | S | H | O | Me | H | Cl | Me |
| 82 | t-Bu | Cl | S | H | O | Me | H | Br | Me |
| 83 | t-Bu | Cl | S | H | O | Me | H | I | Me |
| 84 | t-Bu | Cl | S | H | O | Me | H | Et | Me |
| 85 | t-Bu | Cl | S | H | O | Me | H | Pr | Me |
| 86 | t-Bu | Cl | S | H | O | Me | H | i-Pr | Me |
| 87 | t-Bu | Cl | S | H | O | Me | H | $CH_2CH=CH_2$ | Me |
| 88 | t-Bu | Cl | S | H | O | Me | H | Bu | Me |
| 89 | t-Bu | Cl | S | H | O | Me | H | i-Bu | Me |
| 90 | t-Bu | Cl | S | H | O | Me | H | $CH_2$—c-Pr | Me |
| 91 | t-Bu | Cl | S | H | O | Me | H | $CH_2C\equiv CH$ | Me |
| 92 | t-Bu | Cl | S | H | O | Me | H | t-Bu | Me |
| 93 | t-Bu | Cl | S | H | O | Me | H | Pen | Me |
| 94 | t-Bu | Cl | S | H | O | Me | H | t-Am | Me |
| 95 | t-Bu | Cl | S | H | O | Me | H | Hex | Me |
| 96 | t-Bu | Cl | S | H | O | Me | H | c-Hex | Me |
| 97 | t-Bu | Cl | S | H | O | Me | H | $(CH_2)_7CH_3$ | Me |
| 98 | t-Bu | Cl | S | H | O | Me | H | $(CH_2)_9CH_3$ | Me |
| 99 | t-Bu | Cl | S | H | O | Me | H | $CH_2$—c-Hex | Me |
| 100 | t-Bu | Cl | S | H | O | Me | H | Ph | Me |
| 102 | t-Bu | Cl | S | H | O | Me | H | $NO_2$ | Me |
| 103 | t-Bu | Cl | S | H | O | Me | H | COOMe | Me |
| 104 | t-Bu | Cl | S | H | O | Me | H | COOEt | Me |
| 105 | t-Bu | Cl | S | H | O | Me | H | COOPr | Me |
| 106 | t-Bu | Cl | S | H | O | Me | H | $CH_2CF_3$ | Me |
| 107 | t-Bu | Cl | S | H | O | Me | H | $CH_2CH_2CF_3$ | Me |
| 108 | t-Bu | Cl | S | H | O | Me | H | $NMe_2$ | Me |
| 109 | t-Bu | Cl | S | H | O | Me | H | $NEt_2$ | Me |

TABLE 1-continued

| No. | R | A | X | R$^1$ | Y | Z$^1$ | Z$^2$ | Z$^3$ | Z$^4$ |
|---|---|---|---|---|---|---|---|---|---|
| 110 | t-Bu | Cl | S | H | O | Me | H | NPr$_2$ | Me |
| 111 | t-Bu | Cl | S | H | O | Me | H | OMe | Me |
| 112 | t-Bu | Cl | S | H | O | Me | H | OEt | Me |
| 113 | t-Bu | Cl | S | H | O | Me | H | OPr | Me |
| 114 | t-Bu | Cl | S | H | O | Me | H | O—i-Pr | Me |
| 115 | t-Bu | Cl | S | H | O | Me | H | OBu | Me |
| 116 | t-Bu | Cl | S | H | O | Me | H | O—t-Bu | Me |
| 117 | t-Bu | Cl | S | H | O | Me | H | OPen | Me |
| 118 | t-Bu | Cl | S | H | O | Me | H | O—c-Hex | Me |
| 119 | t-Bu | Cl | S | H | O | Me | H | OCH$_2$CH=CH$_2$ | Me |
| 120 | t-Bu | Cl | S | H | O | Me | H | OCH$_2$C≡CH | Me |
| 121 | t-Bu | Br | S | H | O | Me | H | COCH$_2$CH$_3$ | Me |
| 122 | t-Bu | OMe | S | H | O | Me | H | COCH$_2$CH$_3$ | Me |
| 123 | t-Bu | SMe | S | H | O | Me | H | COCH$_2$CH$_3$ | Me |
| 124 | t-Bu | Br | S | H | O | Me | H | Pr | Me |
| 125 | t-Bu | OMe | S | H | O | Me | H | Pr | Me |
| 126 | t-Bu | SMe | S | H | O | Me | H | Pr | Me |
| 127 | t-Bu | Cl | S | H | O | Me | H | SMe | Me |
| 128 | t-Bu | Cl | S | H | O | Me | H | SEt | Me |
| 129 | t-Bu | Cl | S | H | O | Me | H | SPr | Me |
| 130 | t-Bu | Cl | S | H | O | Me | H | SOMe | Me |
| 131 | t-Bu | Cl | S | H | O | Me | H | SOEt | Me |
| 132 | t-Bu | Cl | S | H | O | Me | H | SOPr | Me |
| 133 | t-Bu | Cl | S | H | O | Me | H | SO$_2$Me | Me |
| 134 | t-Bu | Cl | S | H | O | Me | H | SO$_2$Et | Me |
| 135 | t-Bu | Cl | S | H | O | Me | H | SO$_2$Pr | Me |
| 136 | t-Bu | Cl | S | H | O | Me | H | SCH$_2$CH=CH$_2$ | Me |
| 137 | t-Bu | Cl | S | H | O | Me | H | SCH$_2$C≡CH | Me |
| 138 | t-Bu | Cl | S | H | O | Me | H | SOCH$_2$CH=CH$_2$ | Me |
| 139 | t-Bu | Cl | S | H | O | Me | H | SOCH$_2$C≡CH | Me |
| 140 | t-Bu | Cl | S | H | O | Me | H | SO$_2$CH$_2$CH=CH$_2$ | Me |
| 141 | t-Bu | Cl | S | H | O | Me | H | SO$_2$CH$_2$C≡CH | Me |
| 142 | t-Bu | Cl | S | H | O | Me | H | S—i-Pr | Me |
| 143 | t-Bu | Cl | S | H | O | Me | H | S—t-Br | Me |
| 144 | t-Bu | Cl | S | H | O | Me | H | S—c-Hex | Me |
| 145 | t-Bu | Cl | S | H | O | Me | H | SO$_2$—i-Pr | Me |
| 146 | t-Bu | Cl | S | H | O | Me | H | SO$_2$—t-Bu | Me |
| 147 | t-Bu | Cl | S | H | O | Me | H | SO—c-Hex | Me |
| 148 | t-Bu | Cl | S | H | O | Cl | Et | Cl | Cl |
| 149 | t-Bu | Cl | S | H | O | Cl | Pr | Cl | Cl |
| 150 | t-Bu | Cl | S | H | O | Cl | t-Bu | Cl | Cl |
| 151 | t-Bu | Cl | S | H | S | H | H | t-Bu | H |
| 152 | t-Bu | Cl | S | H | S | Me | H | H | Me |
| 153 | t-Bu | Cl | S | H | S | Me | H | Me | Me |
| 154 | t-Bu | Cl | S | H | S | Me | H | COCH$_2$CH$_3$ | Me |
| 155 | t-Bu | Cl | S | H | S | Me | H | Pr | Me |
| 156 | t-Bu | Cl | S | H | S | Me | H | OEt | Me |
| 161 | t-Bu | Cl | S | H | CH$_2$ | H | H | t-Bu | H |
| 162 | t-Bu | Cl | S | H | CH$_2$ | Me | H | H | Me |
| 163 | t-Bu | Cl | S | H | CH$_2$ | Me | H | COCH$_2$CH$_3$ | Me |
| 164 | t-Bu | Cl | S | H | CH$_2$ | Me | H | Pr | Me |
| 165 | t-Bu | Cl | S | H | CH$_2$ | Me | H | OEt | Me |
| 171 | t-Bu | Cl | S | Me | O | H | H | t-Bu | H |
| 172 | t-Bu | Cl | S | Me | O | Me | H | H | Me |
| 173 | t-Bu | Cl | S | Me | O | Me | H | COCH$_2$CH$_3$ | Me |
| 174 | t-Bu | Cl | S | Me | O | Me | H | Pr | Me |
| 175 | t-Bu | Cl | S | Me | O | Me | H | OEt | Me |
| 198 | t-Bu | Cl | O | H | S | Me | H | H | Me |
| 199 | t-Bu | Cl | O | H | S | Me | H | Me | Me |
| 219 | t-Bu | Cl | O | H | O | Me | H | Me | Me |
| 223 | t-Bu | Cl | O | H | O | OMe | H | H | OMe |
| 224 | t-Bu | Cl | O | H | O | Me | H | H | Cl |
| 225 | t-Bu | Cl | O | H | O | Cl | H | H | Cl |
| 226 | t-Bu | Cl | O | H | O | Me | H | Cl | Cl |
| 227 | Pr | Cl | O | H | O | Me | H | Cl | Cl |
| 228 | t-Bu | Cl | O | H | O | Me | Me | H | Me |
| 229 | t-Bu | Cl | O | H | O | Me | H | Me | Me |
| 230 | t-Bu | Cl | O | H | O | Me | H | Br | Cl |
| 231 | t-Bu | Cl | O | H | O | Me | H | COCH$_2$CH$_3$ | Cl |
| 232 | t-Bu | Cl | O | H | O | Me | H | Pr | Cl |

TABLE 1-continued

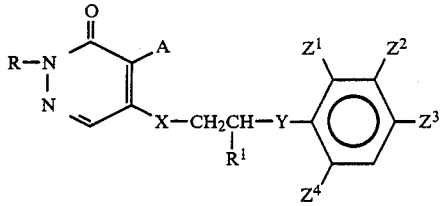

| No. | R | A | X | R¹ | Y | Z¹ | Z² | Z³ | Z⁴ |
|---|---|---|---|---|---|---|---|---|---|
| 233 | t-Bu | Cl | O | H | O | Cl | H | COCH$_2$CH$_3$ | Cl |
| 234 | t-Bu | Cl | O | H | O | Cl | H | Et | Cl |
| 235 | t-Bu | Cl | O | H | O | Cl | H | Pr | Cl |
| 236 | t-Bu | Cl | O | H | O | Cl | H | i-Pr | Cl |
| 237 | t-Bu | Cl | O | H | O | Cl | H | Bu | Cl |
| 238 | t-Bu | Cl | O | H | O | Cl | H | i-Bu | Cl |
| 239 | t-Bu | Cl | O | H | O | Cl | H | t-Bu | Cl |
| 240 | t-Bu | Cl | O | H | O | Cl | H | Pen | Cl |
| 241 | t-Bu | Cl | O | H | O | Cl | H | Ph | Cl |
| 242 | t-Bu | Cl | O | H | O | Br | H | COCH$_2$CH$_3$ | Br |
| 243 | t-Bu | Cl | O | H | O | Br | H | Et | Br |
| 244 | t-Bu | Cl | O | H | O | Br | H | Pr | Br |
| 245 | t-Bu | Cl | O | H | O | Br | H | i-Pr | Br |
| 246 | t-Bu | Cl | O | H | O | Br | H | Bu | Br |
| 247 | t-Bu | Cl | O | H | O | Br | H | i-Bu | Br |
| 248 | t-Bu | Cl | O | H | O | Br | H | t-Bu | Br |
| 249 | t-Bu | Cl | O | H | O | Br | H | Ph | Br |
| 250 | t-Bu | Cl | O | H | O | F | H | COCH$_2$CH$_3$ | F |
| 251 | t-Bu | Cl | O | H | O | F | H | CH=CHCH$_3$ | F |
| 252 | t-Bu | Cl | O | H | O | F | H | Pr | F |
| 253 | t-Bu | Cl | O | H | O | F | H | Bu | F |
| 254 | t-Bu | Cl | O | H | O | F | H | Pen | F |
| 255 | t-Bu | Cl | O | H | O | F | H | Et | F |
| 256 | t-Bu | Cl | O | H | O | NO$_2$ | H | Me | NO$_2$ |
| 257 | t-Bu | Cl | O | H | O | NO$_2$ | H | Et | NO$_2$ |
| 258 | t-Bu | Cl | O | H | O | NO$_2$ | H | Pr | NO$_2$ |
| 259 | t-Bu | Cl | O | H | O | NO$_2$ | H | Bu | NO$_2$ |
| 260 | t-Bu | Cl | O | H | O | NO$_2$ | H | Pen | NO$_2$ |
| 261 | t-Bu | Cl | O | H | O | OMe | H | Et | OMe |
| 262 | t-Bu | Cl | O | H | O | OMe | H | Pr | OMe |
| 263 | t-Bu | Cl | O | H | O | OMe | H | i-Pr | OMe |
| 264 | t-Bu | Cl | O | H | O | OMe | H | Bu | OMe |
| 265 | t-Bu | Cl | O | H | O | OMe | H | t-Bu | OMe |
| 266 | t-Bu | Cl | O | H | O | Me | H | COCH$_3$ | Me |
| 267 | t-Bu | Cl | O | H | O | Me | H | COCH$_2$CH$_3$ | Me |
| 268 | t-Bu | Cl | O | H | O | Me | H | COCH$_2$CH$_2$CH$_3$ | Me |
| 269 | t-Bu | Cl | O | H | O | Me | H | COCH(CH$_3$)$_2$ | Me |
| 270 | t-Bu | Cl | O | H | O | Me | H | CO—c-Pr | Me |
| 271 | t-Bu | Cl | O | H | O | Me | H | CO(CH$_2$)$_3$CH$_3$ | Me |
| 272 | t-Bu | Cl | O | H | O | Me | H | CO—c-Hex | Me |
| 273 | t-Bu | Cl | O | H | O | Me | H | CO(CH$_2$)$_4$CH$_3$ | Me |
| 274 | t-Bu | Cl | O | H | O | Me | H | CO(CH$_2$)$_6$CH$_3$ | Me |
| 275 | t-Bu | Cl | O | H | O | Me | H | CO(CH$_3$)$_8$CH$_3$ | Me |
| 276 | t-Bu | Cl | O | H | O | Me | H | Cl | Me |
| 277 | t-Bu | Cl | O | H | O | Me | H | Br | Me |
| 278 | t-Bu | Cl | O | H | O | Me | H | I | Me |
| 279 | t-Bu | Cl | O | H | O | Me | H | Et | Me |
| 280 | t-Bu | Cl | O | H | O | Me | H | Pr | Me |
| 281 | t-Bu | Cl | O | H | O | Me | H | i-Pr | Me |
| 282 | t-Bu | Cl | O | H | O | Me | H | CH$_2$CH=CH$_2$ | Me |
| 283 | t-Bu | Cl | O | H | O | Me | H | Bu | Me |
| 284 | t-Bu | Cl | O | H | O | Me | H | i-Bu | Me |
| 285 | t-Bu | Cl | O | H | O | Me | H | CH$_2$—c-Pr | Me |
| 286 | t-Bu | Cl | O | H | O | Me | H | CH$_2$C≡CH | Me |
| 287 | t-Bu | Cl | O | H | O | Me | H | t-Bu | Me |
| 288 | t-Bu | Cl | O | H | O | Me | H | Pen | Me |
| 289 | t-Bu | Cl | O | H | O | Me | H | t-Am | Me |
| 290 | t-Bu | Cl | O | H | O | Me | H | Hex | Me |
| 291 | t-Bu | Cl | O | H | O | Me | H | c-Hex | Me |
| 292 | t-Bu | Cl | O | H | O | Me | H | (CH$_2$)$_7$CH$_3$ | Me |
| 293 | t-Bu | Cl | O | H | O | Me | H | (CH$_2$)$_9$CH$_3$ | Me |
| 294 | t-Bu | Cl | O | H | O | Me | H | CH$_2$—c-Hex | Me |
| 295 | t-Bu | Cl | O | H | O | Me | H | Ph | Me |
| 296 | t-Bu | Cl | O | H | O | Me | H | NO$_2$ | Me |
| 298 | t-Bu | Cl | O | H | O | Me | H | COOMe | Me |
| 299 | t-Bu | Cl | O | H | O | Me | H | COOEt | Me |
| 300 | t-Bu | Cl | O | H | O | Me | H | COOPr | Me |
| 301 | t-Bu | Cl | O | H | O | Me | H | CH$_2$CF$_3$ | Me |
| 302 | t-Bu | Cl | O | H | O | Me | H | CH$_2$CH$_2$CF$_3$ | Me |
| 303 | t-Bu | Cl | O | H | O | Me | H | NMe$_2$ | Me |

TABLE 1-continued

Structure: R-N(-N=)-C(=O)-C(A)=C(-X-CH2CH(R1)-Y-Ar)-CH= (pyridazinone) with Ar = phenyl substituted by Z1, Z2, Z3, Z4

| No. | R | A | X | R¹ | Y | Z¹ | Z² | Z³ | Z⁴ |
|---|---|---|---|---|---|---|---|---|---|
| 304 | t-Bu | Cl | O | H | O | Me | H | NEt₂ | Me |
| 305 | t-Bu | Cl | O | H | O | Me | H | NPr₂ | Me |
| 306 | t-Bu | Cl | O | H | O | Me | H | OMe | Me |
| 307 | t-Bu | Cl | O | H | O | Me | H | OEt | Me |
| 308 | t-Bu | Cl | O | H | O | Me | H | OPr | Me |
| 309 | t-Bu | Cl | O | H | O | Me | H | O—i-Pr | Me |
| 310 | t-Bu | Cl | O | H | O | Me | H | OBu | Me |
| 311 | t-Bu | Cl | O | H | O | Me | H | O—t-Bu | Me |
| 312 | t-Bu | Cl | O | H | O | Me | H | OPen | Me |
| 313 | t-Bu | Cl | O | H | O | Me | H | O—c-Hex | Me |
| 314 | t-Bu | Cl | O | H | O | Me | H | OCH₂CH=CH₂ | Me |
| 315 | t-Bu | Cl | O | H | O | Me | H | OCH₂C≡CH₃ | Me |
| 316 | t-Bu | Br | O | H | O | Me | H | COCH₂CH₃ | Me |
| 317 | t-Bu | OMe | O | H | O | Me | H | COCH₂CH₃ | Me |
| 318 | t-Bu | SMe | O | H | O | Me | H | COCH₂CH₃ | Me |
| 319 | t-Bu | Br | O | H | O | Me | H | Pr | Me |
| 320 | t-Bu | OMe | O | H | O | Me | H | Pr | Me |
| 321 | t-Bu | SMe | O | H | O | Me | H | Pr | Me |
| 322 | t-Bu | Cl | O | H | O | Me | H | SMe | Me |
| 323 | t-Bu | Cl | O | H | O | Me | H | SEt | Me |
| 324 | t-Bu | Cl | O | H | O | Me | H | SPr | Me |
| 325 | t-Bu | Cl | O | H | O | Me | H | SOMe | Me |
| 326 | t-Bu | Cl | O | H | O | Me | H | SOEt | Me |
| 327 | t-Bu | Cl | O | H | O | Me | H | SOPr | Me |
| 328 | t-Bu | Cl | O | H | O | Me | H | SO₂Me | Me |
| 329 | t-Bu | Cl | O | H | O | Me | H | SO₂Et | Me |
| 330 | t-Bu | Cl | O | H | O | Me | H | SO₂Pr | Me |
| 331 | t-Bu | Cl | O | H | O | Me | H | SCH₂CH=CH₂ | Me |
| 332 | t-Bu | Cl | O | H | O | Me | H | SCH₂C≡CH₃ | Me |
| 333 | t-Bu | Cl | O | H | O | Me | H | SOCH₂CH=CH₂ | Me |
| 334 | t-Bu | Cl | O | H | O | Me | H | SOCH₂C≡CH₃ | Me |
| 335 | t-Bu | Cl | O | H | O | Me | H | SO₂CH₂CH=CH₂ | Me |
| 336 | t-Bu | Cl | O | H | O | Me | H | SO₂CH₂C≡CH₃ | Me |
| 337 | t-Bu | Cl | O | H | O | Me | H | S—i-Pr | Me |
| 338 | t-Bu | Cl | O | H | O | Me | H | S—t-Bu | Me |
| 339 | t-Bu | Cl | O | H | O | Me | H | S—c-Hex | Me |
| 340 | t-Bu | Cl | O | H | O | Me | H | SO₂—i-Pr | Me |
| 341 | t-Bu | Cl | O | H | O | Me | H | SO₂—t-Bu | Me |
| 342 | t-Bu | Cl | O | H | O | Me | H | SO₂—c-Hex | Me |
| 343 | t-Bu | Cl | O | H | O | Cl | Et | Cl | Cl |
| 344 | t-Bu | Cl | O | H | O | Cl | t-Bu | Cl | Cl |
| 360 | t-Bu | Cl | O | Me | O | Me | H | Pr | Me |

TABLE 2

Structure: pyridazinone linked via X—CH2CH(R1)—Y to biphenyl ether system with Z5, Q, Z6n substituents

| No. | R | A | X | R¹ | Y | Z⁵ | Q | Z⁶ₙ |
|---|---|---|---|---|---|---|---|---|
| 421 | t-Bu | Cl | S | H | O | H | O | H |
| 422 | t-Bu | Cl | S | H | O | H | O | 4-Cl |
| 423 | t-Bu | Cl | S | H | O | H | O | 4-Me |
| 424 | t-Bu | Cl | S | H | O | Cl | O | H |
| 425 | t-Bu | Cl | S | H | O | Cl | O | 4-Me |
| 426 | t-Bu | Cl | S | H | O | Me | O | H |
| 427 | t-Bu | Cl | S | H | O | Me | O | 4-Cl |
| 428 | t-Bu | Cl | S | H | O | Me | O | 2-Me |
| 429 | t-Bu | Cl | S | H | O | Me | O | 4-Me |
| 430 | t-Bu | Cl | S | H | O | Me | O | 4-Et |
| 431 | t-Bu | Cl | S | H | O | Me | O | 4-t-Bu |
| 432 | t-Bu | Cl | S | H | O | Me | O | 4-OMe |

TABLE 2-continued

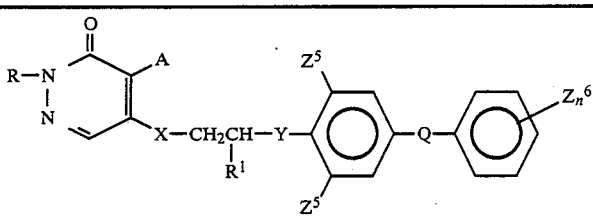

| No. | R | A | X | R¹ | Y | Z⁵ | Q | Z⁶ₙ |
|-----|---|---|---|----|----|----|---|-----|
| 433 | t-Bu | Cl | S | H | O | Me | O | 4-CF$_3$ |
| 434 | t-Bu | Cl | S | H | O | Me | O | 4-NO$_2$ |
| 435 | t-Bu | Cl | S | H | O | Me | O | 4-CN |
| 436 | t-Bu | Cl | S | H | O | Me | O | 4-OCF$_3$ |
| 437 | t-Bu | Cl | S | H | O | Me | O | 2-Cl,4-Cl |
| 438 | t-Bu | Cl | S | H | O | Me | O | 2-Me,4-Me |
| 439 | t-Bu | Cl | S | H | O | Me | O | 2-Cl,4-Cl,6-Cl |
| 440 | t-Bu | Cl | S | H | O | Me | O | 2-Me,4-Me,6-Me |
| 441 | t-Bu | Cl | S | H | O | H | S | H |
| 442 | t-Bu | Cl | S | H | O | H | S | 4-Me |
| 443 | t-Bu | Cl | S | H | O | Me | S | H |
| 444 | t-Bu | Cl | S | H | O | Me | S | 4-F |
| 445 | t-Bu | Cl | S | H | O | Me | S | 4-Cl |
| 446 | t-Bu | Cl | S | H | O | Me | SO | 4-Cl |
| 447 | t-Bu | Cl | S | H | O | Me | SO$_2$ | 4-Cl |
| 448 | t-Bu | Cl | S | H | O | Me | S | 4-Me |
| 449 | t-Bu | Cl | S | H | O | Me | SO | 4-Me |
| 450 | t-Bu | Cl | S | H | O | Me | SO$_2$ | 4-Me |
| 451 | t-Bu | Cl | S | H | O | H | NH | H |
| 452 | t-Bu | Cl | S | H | O | H | NH | 4-Cl |
| 453 | t-Bu | Cl | S | H | O | Me | NH | H |
| 454 | t-Bu | Cl | S | H | O | Me | NH | 4-Cl |
| 455 | t-Bu | Cl | S | H | O | Me | NMe | H |
| 456 | t-Bu | Cl | S | H | O | Me | NMe | 4-Cl |
| 457 | t-Bu | Cl | S | H | O | Me | NCOMe | H |
| 458 | t-Bu | Cl | S | H | O | Me | NCOMe | 4-Cl |
| 459 | t-Bu | Cl | S | H | O | H | CO | H |
| 460 | t-Bu | Cl | S | H | O | H | CO | 4-Cl |
| 461 | t-Bu | Cl | S | H | O | H | CO | 4-Me |
| 462 | t-Bu | Cl | S | H | O | Cl | CO | H |
| 463 | t-Bu | Cl | S | H | O | Cl | CO | 4-Cl |
| 464 | t-Bu | Cl | S | H | O | Cl | CO | 4-Me |
| 465 | t-Bu | Cl | S | H | O | Me | CO | H |
| 466 | t-Bu | Cl | S | H | O | Me | CO | 2-Cl |
| 467 | t-Bu | Cl | S | H | O | Me | CO | 3-Cl |
| 468 | t-Bu | Cl | S | H | O | Me | CO | 4-Cl |
| 469 | t-Bu | Cl | S | H | O | Me | CO | 2-F |
| 470 | t-Bu | Cl | S | H | O | Me | CO | 4-F |
| 471 | t-Bu | Cl | S | H | O | Me | CO | 2-Br |
| 472 | t-Bu | Cl | S | H | O | Me | CO | 4-Br |
| 473 | t-Bu | Cl | S | H | O | Me | CO | 4-I |
| 474 | t-Bu | Cl | S | H | O | Me | CO | 2-Me |
| 475 | t-Bu | Cl | S | H | O | Me | CO | 3-Me |
| 476 | t-Bu | Cl | S | H | O | Me | CO | 4-Me |
| 477 | t-Bu | Cl | S | H | O | Me | CO | 4-Et |
| 478 | t-Bu | Cl | S | H | O | Me | CO | 4-Bu |
| 479 | t-Bu | Cl | S | H | O | Me | CO | 4-i-Pr |
| 480 | t-Bu | Cl | S | H | O | Me | CO | 4-t-Bu |
| 481 | t-Bu | Cl | S | H | O | Me | CO | 4-CF$_3$ |
| 482 | t-Bu | Cl | S | H | O | Me | CO | 4-NO$_2$ |
| 483 | t-Bu | Cl | S | H | O | Me | CO | 4-CN |
| 484 | t-Bu | Cl | S | H | O | Me | CO | 4-OMe |
| 485 | t-Bu | Cl | S | H | O | Me | CO | 4-OEt |
| 486 | t-Bu | Cl | S | H | O | Me | CO | 4-SMe |
| 487 | t-Bu | Cl | S | H | O | Me | CO | 4-NMe$_2$ |
| 488 | t-Bu | Cl | S | H | O | Me | CO | 2-F,4-F |
| 489 | t-Bu | Cl | S | H | O | Me | CO | 2-F,6-F |
| 490 | t-Bu | Cl | S | H | O | Me | CO | 2-Cl,4-Cl |
| 491 | t-Bu | Cl | S | H | O | Me | CO | 2-Cl,6-Cl |
| 492 | t-Bu | Cl | S | H | O | Me | CO | 3-Cl,4-Cl |
| 493 | t-Bu | Cl | S | H | O | Me | CO | 3-Cl,5-Cl |
| 494 | t-Bu | Cl | S | H | O | Me | CO | 2-Cl,4-NO$_2$ |
| 495 | t-Bu | Cl | S | H | O | Me | CO | 2-NO$_2$,4-Cl |
| 496 | t-Bu | Cl | S | H | O | Me | CO | 2-Me,4-Me |
| 497 | t-Bu | Cl | S | H | O | Me | CO | 2-Me,6-Me |
| 498 | t-Bu | Cl | S | H | O | Me | CO | 3-Me,4-Me |
| 499 | t-Bu | Cl | S | H | O | Me | CO | 3-Me,5-Me |
| 500 | t-Bu | Cl | S | H | O | Me | CO | 3,4-CH=CHCH=CH— |
| 501 | t-Bu | Cl | S | H | O | Me | CO | 2-Cl,4-Me |
| 502 | t-Bu | Cl | S | H | O | Me | CO | 2-Cl,6-Me |

TABLE 2-continued

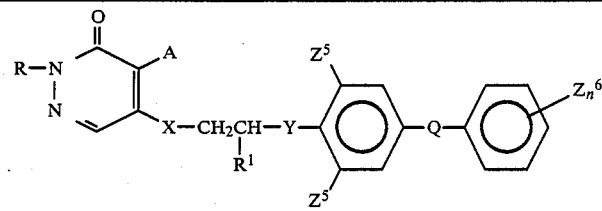

| No. | R | A | X | R¹ | Y | Z⁵ | Q | Z⁶$_n$ |
|---|---|---|---|---|---|---|---|---|
| 503 | t-Bu | Cl | S | H | O | Me | CO | 2-Me,4-Cl |
| 504 | t-Bu | Cl | S | H | O | Me | CO | 2-Cl,4-Cl,6-Cl |
| 505 | t-Bu | Cl | S | H | O | Me | CO | 2-Me,4-Me,5-Me |
| 506 | t-Bu | Cl | S | H | O | Me | CO | 2-Me,4-Me,6-Me |
| 507 | t-Bu | Br | S | H | O | Me | CO | H |
| 508 | t-Bu | OMe | S | H | O | Me | CO | H |
| 509 | t-Bu | SMe | S | H | O | Me | CO | H |
| 510 | t-Bu | Cl | S | H | O | i-Pr | CO | H |
| 511 | t-Bu | Cl | S | H | O | H | CH$_2$ | H |
| 512 | t-Bu | Cl | S | H | O | H | CH$_2$ | 4-Cl |
| 513 | t-Bu | Cl | S | H | O | H | CH$_2$ | 4-Me |
| 514 | t-Bu | Cl | S | H | O | Cl | CH$_2$ | H |
| 515 | t-Bu | Cl | S | H | O | Cl | CH$_2$ | 4-Cl |
| 516 | t-Bu | Cl | S | H | O | Cl | CH$_2$ | 4-Me |
| 517 | t-Bu | Cl | S | H | O | Me | CH$_2$ | H |
| 518 | t-Bu | Cl | S | H | O | Me | CH$_2$ | 2-Cl |
| 619 | t-Bu | Cl | S | H | O | Me | CH$_2$ | 3-Cl |
| 520 | t-Bu | Cl | S | H | O | Me | CH$_2$ | 4-Cl |
| 521 | t-Bu | Cl | S | H | O | Me | CH$_2$ | 2-F |
| 522 | t-Bu | Cl | S | H | O | Me | CH$_2$ | 4-F |
| 523 | t-Bu | Cl | S | H | O | Me | CH$_2$ | 2-Br |
| 524 | t-Bu | Cl | S | H | O | Me | CH$_2$ | 4-Br |
| 525 | t-Bu | Cl | S | H | O | Me | CH$_2$ | 4-I |
| 526 | t-Bu | Cl | S | H | O | Me | CH$_2$ | 2-Me |
| 527 | t-Bu | Cl | S | H | O | Me | CH$_2$ | 3-Me |
| 528 | t-Bu | Cl | S | H | O | Me | CH$_2$ | 4-Me |
| 529 | t-Bu | Cl | S | H | O | Me | CH$_2$ | 4-Et |
| 530 | t-Bu | Cl | S | H | O | Me | CH$_2$ | 4-Bu |
| 531 | t-Bu | Cl | S | H | O | Me | CH$_2$ | 4-i-Pr |
| 532 | t-Bu | Cl | S | H | O | Me | CH$_2$ | 4-t-Bu |
| 533 | t-Bu | Cl | S | H | O | Me | CH$_2$ | 4-CF$_3$ |
| 534 | t-Bu | Cl | S | H | O | Me | CH$_2$ | 4-NO$_2$ |
| 535 | t-Bu | Cl | S | H | O | Me | CH$_2$ | 4-CN |
| 536 | t-Bu | Cl | S | H | O | Me | CH$_2$ | 4-OMe |
| 537 | t-Bu | Cl | S | H | O | Me | CH$_2$ | 4-OEt |
| 538 | t-Bu | Cl | S | H | O | Me | CH$_2$ | 4-SMe |
| 539 | t-Bu | Cl | S | H | O | Me | CH$_2$ | 4-NMe$_2$ |
| 540 | t-Bu | Cl | S | H | O | Me | CH$_2$ | 2-F,4-F |
| 541 | t-Bu | Cl | S | H | O | Me | CH$_2$ | 2-F,6-F |
| 542 | t-Bu | Cl | S | H | O | Me | CH$_2$ | 2-Cl,4-Cl |
| 543 | t-Bu | Cl | S | H | O | Me | CH$_2$ | 2-Cl,6-Cl |
| 544 | t-Bu | Cl | S | H | O | Me | CH$_2$ | 3-Cl,4-Cl |
| 545 | t-Bu | Cl | S | H | O | Me | CH$_2$ | 3-Cl,5-Cl |
| 546 | t-Bu | Cl | S | H | O | Me | CH$_2$ | 2-Cl,4-NO$_2$ |
| 547 | t-Bu | Cl | S | H | O | Me | CH$_2$ | 2-NO$_2$,4-Cl |
| 548 | t-Bu | Cl | S | H | O | Me | CH$_2$ | 2-Me,4-Me |
| 549 | t-Bu | Cl | S | H | O | Me | CH$_2$ | 2-Me,6-Me |
| 550 | t-Bu | Cl | S | H | O | Me | CH$_2$ | 3-Me,4-Me |
| 551 | t-Bu | Cl | S | H | O | Me | CH$_2$ | 3-Me,5-Me |
| 552 | t-Bu | Cl | S | H | O | Me | CH$_2$ | 3,4-CH=CHCH=CH— |
| 553 | t-Bu | Cl | S | H | O | Me | CH$_2$ | 2-Cl,4-Me |
| 554 | t-Bu | Cl | S | H | O | Me | CH$_2$ | 2-Cl,6-Me |
| 555 | t-Bu | Cl | S | H | O | Me | CH$_2$ | 2-Me,4-Cl |
| 556 | t-Bu | Cl | S | H | O | Me | CH$_2$ | 2-Cl,4-Cl,6-Cl |
| 557 | t-Bu | Cl | S | H | O | Me | CH$_2$ | 2-Me,4-Me,5-Me |
| 558 | t-Bu | Cl | S | H | O | Me | CH$_2$ | 2-Me,4-Me,6-Me |
| 559 | t-Bu | Br | S | H | O | Me | CH$_2$ | H |
| 560 | t-Bu | OMe | S | H | O | Me | CH$_2$ | H |
| 561 | t-Bu | SMe | S | H | O | Me | CH$_2$ | H |
| 562 | t-Bu | Cl | S | H | O | i-Pr | CH$_2$ | H |
| 563 | t-Bu | Cl | S | H | O | Me | CHMe | H |
| 564 | t-Bu | Cl | S | H | O | Me | CHMe | 4-Cl |
| 565 | t-Bu | Cl | S | H | O | Me | CHMe | 4-Me |
| 566 | t-Bu | Cl | S | H | O | Me | CHMe | 4-OMe |
| 567 | t-Bu | Cl | S | H | O | i-Pr | CHMe | H |
| 568 | t-Bu | Cl | S | H | O | i-Pr | CHMe | 4-Cl |
| 569 | t-Bu | Cl | S | H | O | i-Pr | CHMe | 4-Me |
| 570 | t-Bu | Cl | S | H | O | i-Pr | CHMe | 4-OMe |
| 575 | t-Bu | Cl | S | H | O | H | OCH$_2$ | H |
| 576 | t-Bu | Cl | S | H | O | H | OCH$_2$ | 4-Cl |

TABLE 2-continued

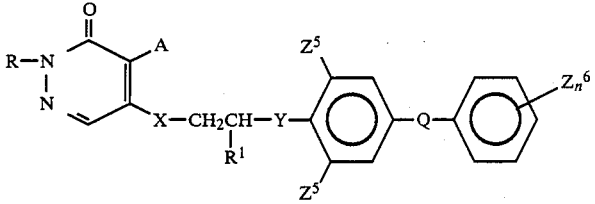

| No. | R | A | X | $R^1$ | Y | $Z^5$ | Q | $Z^6_n$ |
|---|---|---|---|---|---|---|---|---|
| 577 | t-Bu | Cl | S | H | O | H | OCH$_2$ | 4-Me |
| 578 | t-Bu | Cl | S | H | O | H | OCH$_2$ | 4-OMe |
| 579 | t-Bu | Cl | S | H | O | H | COCH$_2$ | H |
| 583 | t-Bu | Cl | S | H | O | Cl | COCH$_2$ | H |
| 587 | t-Bu | Cl | S | H | O | Br | COCH$_2$ | H |
| 589 | t-Bu | Cl | S | H | O | Me | COCH$_2$ | H |
| 593 | t-Bu | Cl | S | H | O | H | CH$_2$CH$_2$ | H |
| 597 | t-Bu | Cl | S | H | O | Me | CH$_2$CH$_2$ | H |
| 604 | t-Bu | Cl | O | H | O | Cl | O | H |
| 605 | t-Bu | Cl | O | H | O | Cl | O | 4-Me |
| 606 | t-Bu | Cl | O | H | O | Me | O | H |
| 607 | t-Bu | Cl | O | H | O | Me | O | 4-Cl |
| 608 | t-Bu | Cl | O | H | O | Me | O | 2-Me |
| 609 | t-Bu | Cl | O | H | O | Me | O | 4-Me |
| 610 | t-Bu | Cl | O | H | O | Me | O | 4-Et |
| 611 | t-Bu | Cl | O | H | O | Me | O | 4-t-Bu |
| 612 | t-Bu | Cl | O | H | O | Me | O | 4-OMe |
| 613 | t-Bu | Cl | O | H | O | Me | O | 4-CF$_3$ |
| 614 | t-Bu | Cl | O | H | O | Me | O | 4-NO$_2$ |
| 615 | t-Bu | Cl | O | H | O | Me | O | 4-CN |
| 616 | t-Bu | Cl | O | H | O | Me | O | 4-OCF$_3$ |
| 617 | t-Bu | Cl | O | H | O | Me | O | 2-Cl,4-Cl |
| 618 | t-Bu | Cl | O | H | O | Me | O | 2-Me,4-Me |
| 619 | t-Bu | Cl | O | H | O | Me | O | 2-Cl,4-Cl,6-Cl |
| 620 | t-Bu | Cl | O | H | O | Me | O | 2-Me,4-Me,6-Me |
| 623 | t-Bu | Cl | O | H | O | Me | S | H |
| 624 | t-Bu | Cl | O | H | O | Me | S | 4-F |
| 625 | t-Bu | Cl | O | H | O | Me | S | 4-Cl |
| 626 | t-Bu | Cl | O | H | O | Me | SO | 4-Cl |
| 627 | t-Bu | Cl | O | H | O | Me | SO$_2$ | 4-Cl |
| 628 | t-Bu | Cl | O | H | O | Me | S | 4-Me |
| 629 | t-Bu | Cl | O | H | O | Me | SO | 4-Me |
| 630 | t-Bu | Cl | O | H | O | Me | SO$_2$ | 4-Me |
| 633 | t-Bu | Cl | O | H | O | Me | NH | H |
| 634 | t-Bu | Cl | O | H | O | Me | NH | 4-Cl |
| 635 | t-Bu | Cl | O | H | O | Me | NH | 4-Me |
| 636 | t-Bu | Cl | O | H | O | Me | NMe | H |
| 637 | t-Bu | Cl | O | H | O | Me | NMe | 4-Cl |
| 638 | t-Bu | Cl | O | H | O | Me | NMe | 4-Me |
| 642 | t-Bu | Cl | O | H | O | Cl | CO | H |
| 643 | t-Bu | Cl | O | H | O | Cl | CO | 4-Cl |
| 644 | t-Bu | Cl | O | H | O | Cl | CO | 4-Me |
| 645 | t-Bu | Cl | O | H | O | Me | CO | H |
| 646 | t-Bu | Cl | O | H | O | Me | CO | 2-Cl |
| 647 | t-Bu | Cl | O | H | O | Me | CO | 3-Cl |
| 648 | t-Bu | Cl | O | H | O | Me | CO | 4-Cl |
| 649 | t-Bu | Cl | O | H | O | Me | CO | 2-F |
| 650 | t-Bu | Cl | O | H | O | Me | CO | 4-F |
| 651 | t-Bu | Cl | O | H | O | Me | CO | 2-Br |
| 652 | t-Bu | Cl | O | H | O | Me | CO | 4-Br |
| 653 | t-Bu | Cl | O | H | O | Me | CO | 4-I |
| 654 | t-Bu | Cl | O | H | O | Me | CO | 2-Me |
| 655 | t-Bu | Cl | O | H | O | Me | CO | 3-Me |
| 656 | t-Bu | Cl | O | H | O | Me | CO | 4-Me |
| 657 | t-Bu | Cl | O | H | O | Me | CO | 4-Et |
| 658 | t-Bu | Cl | O | H | O | Me | CO | 4-Bu |
| 659 | t-Bu | Cl | O | H | O | Me | CO | 4-i-Pr |
| 660 | t-Bu | Cl | O | H | O | Me | CO | 4-t-Bu |
| 661 | t-Bu | Cl | O | H | O | Me | CO | 4-CF$_3$ |
| 662 | t-Bu | Cl | O | H | O | Me | CO | 4-NO$_2$ |
| 663 | t-Bu | Cl | O | H | O | Me | CO | 4-CN |
| 664 | t-Bu | Cl | O | H | O | Me | CO | 4-OMe |
| 665 | t-Bu | Cl | O | H | O | Me | CO | 4-OEt |
| 666 | t-Bu | Cl | O | H | O | Me | CO | 4-SMe |
| 667 | t-Bu | Cl | O | H | O | Me | CO | 4-NMe$_2$ |
| 668 | t-Bu | Cl | O | H | O | Me | CO | 2-F,4-F |
| 669 | t-Bu | Cl | O | H | O | Me | CO | 2-F,6-F |
| 670 | t-Bu | Cl | O | H | O | Me | CO | 2-Cl,4-Cl |
| 671 | t-Bu | Cl | O | H | O | Me | CO | 2-Cl,6-Cl |
| 672 | t-Bu | Cl | O | H | O | Me | CO | 3-Cl,4-Cl |

TABLE 2-continued

| No. | R | A | X | R¹ | Y | Z⁵ | Q | Z⁶$_n$ |
|-----|---|---|---|----|----|----|---|--------|
| 673 | t-Bu | Cl | O | H | O | Me | CO | 3-Cl,5-Cl |
| 674 | t-Bu | Cl | O | H | O | Me | CO | 2-Cl,4-NO$_2$ |
| 675 | t-Bu | Cl | O | H | O | Me | CO | 2-NO$_2$,4-Cl |
| 676 | t-Bu | Cl | O | H | O | Me | CO | 2-Me,4-Me |
| 677 | t-Bu | Cl | O | H | O | Me | CO | 2-Me,6-Me |
| 678 | t-Bu | Cl | O | H | O | Me | CO | 3-Me,4-Me |
| 679 | t-Bu | Cl | O | H | O | Me | CO | 3-Me,5-Me |
| 680 | t-Bu | Cl | O | H | O | Me | CO | 3,4-CH=CHCH=CH— |
| 681 | t-Bu | Cl | O | H | O | Me | CO | 2-Cl,4-Me |
| 682 | t-Bu | Cl | O | H | O | Me | CO | 2-Cl,6-Me |
| 683 | t-Bu | Cl | O | H | O | Me | CO | 2-Me,4-Cl |
| 684 | t-Bu | Cl | O | H | O | Me | CO | 2-Cl,4-Cl,6-Cl |
| 685 | t-Bu | Cl | O | H | O | Me | CO | 2-Me,4-Me,5-Me |
| 686 | t-Bu | Cl | O | H | O | Me | CO | 2-Me,4-Me,6-Me |
| 687 | t-Bu | Br | O | H | O | Me | CO | H |
| 688 | t-Bu | OMe | O | H | O | Me | CO | H |
| 689 | t-Bu | SMe | O | H | O | Me | CO | H |
| 690 | t-Bu | Cl | O | H | O | i-Pr | CO | H |
| 694 | t-Bu | Cl | O | H | O | Cl | CH$_2$ | H |
| 695 | t-Bu | Cl | O | H | O | Cl | CH$_2$ | 4-Cl |
| 696 | t-Bu | Cl | O | H | O | Cl | CH$_2$ | 4-Me |
| 697 | t-Bu | Cl | O | H | O | Me | CH$_2$ | H |
| 698 | t-Bu | Cl | O | H | O | Me | CH$_2$ | 2-Cl |
| 699 | t-Bu | Cl | O | H | O | Me | CH$_2$ | 3-Cl |
| 700 | t-Bu | Cl | O | H | O | Me | CH$_2$ | 4-Cl |
| 701 | t-Bu | Cl | O | H | O | Me | CH$_2$ | 2-F |
| 702 | t-Bu | Cl | O | H | O | Me | CH$_2$ | 4-F |
| 703 | t-Bu | Cl | O | H | O | Me | CH$_2$ | 2-Br |
| 704 | t-Bu | Cl | O | H | O | Me | CH$_2$ | 4-Br |
| 705 | t-Bu | Cl | O | H | O | Me | CH$_2$ | 4-I |
| 706 | t-Bu | Cl | O | H | O | Me | CH$_2$ | 2-Me |
| 707 | t-Bu | Cl | O | H | O | Me | CH$_2$ | 3-Me |
| 708 | t-Bu | Cl | O | H | O | Me | CH$_2$ | 4-Me |
| 709 | t-Bu | Cl | O | H | O | Me | CH$_2$ | 4-Et |
| 710 | t-Bu | Cl | O | H | O | Me | CH$_2$ | 4-Bu |
| 711 | t-Bu | Cl | O | H | O | Me | CH$_2$ | 4-i-Pr |
| 712 | t-Bu | Cl | O | H | O | Me | CH$_2$ | 4-t-Bu |
| 713 | t-Bu | Cl | O | H | O | Me | CH$_2$ | 4-CF$_3$ |
| 714 | t-Bu | Cl | O | H | O | Me | CH$_2$ | 4-NO$_2$ |
| 715 | t-Bu | Cl | O | H | O | Me | CH$_2$ | 4-CN |
| 716 | t-Bu | Cl | O | H | O | Me | CH$_2$ | 4-OMe |
| 717 | t-Bu | Cl | O | H | O | Me | CH$_2$ | 4-OEt |
| 718 | t-Bu | Cl | O | H | O | Me | CH$_2$ | 4-SMe |
| 719 | t-Bu | Cl | O | H | O | Me | CH$_2$ | 4-NMe$_2$ |
| 720 | t-Bu | Cl | O | H | O | Me | CH$_2$ | 2-F,4-F |
| 721 | t-Bu | Cl | O | H | O | Me | CH$_2$ | 2-F,6-F |
| 722 | t-Bu | Cl | O | H | O | Me | CH$_2$ | 2-Cl,4-Cl |
| 723 | t-Bu | Cl | O | H | O | Me | CH$_2$ | 2-Cl,6-Cl |
| 724 | t-Bu | Cl | O | H | O | Me | CH$_2$ | 3-Cl,4-Cl |
| 725 | t-Bu | Cl | O | H | O | Me | CH$_2$ | 3-Cl,5-Cl |
| 726 | t-Bu | Cl | O | H | O | Me | CH$_2$ | 2-Cl,4-NO$_2$ |
| 727 | t-Bu | Cl | O | H | O | Me | CH$_2$ | 2-NO$_2$,4-Cl |
| 728 | t-Bu | Cl | O | H | O | Me | CH$_2$ | 2-Me,4-Me |
| 729 | t-Bu | Cl | O | H | O | Me | CH$_2$ | 2-Me,6-Me |
| 730 | t-Bu | Cl | O | H | O | Me | CH$_2$ | 3-Me,4-Me |
| 731 | t-Bu | Cl | O | H | O | Me | CH$_2$ | 3-Me,5-Me |
| 732 | t-Bu | Cl | O | H | O | Me | CH$_2$ | 3,4-CH=CHCH=CH— |
| 733 | t-Bu | Cl | O | H | O | Me | CH$_2$ | 2-Cl,4-Me |
| 734 | t-Bu | Cl | O | H | O | Me | CH$_2$ | 2-Cl,6-Me |
| 735 | t-Bu | Cl | O | H | O | Me | CH$_2$ | 2-Me,4-Cl |
| 736 | t-Bu | Cl | O | H | O | Me | CH$_2$ | 2-Cl,4-Cl,6-Cl |
| 737 | t-Bu | Cl | O | H | O | Me | CH$_2$ | 2-Me,4-Me,5-Me |
| 738 | t-Bu | Cl | O | H | O | Me | CH$_2$ | 2-Me,4-Me,6-Me |
| 739 | t-Bu | Br | O | H | O | Me | CH$_2$ | H |
| 740 | t-Bu | OMe | O | H | O | Me | CH$_2$ | H |
| 741 | t-Bu | SMe | O | H | O | Me | CH$_2$ | H |
| 742 | t-Bu | Cl | O | H | O | i-Pr | CH$_2$ | H |
| 743 | t-Bu | Cl | O | H | O | Me | CHMe | H |
| 744 | t-Bu | Cl | O | H | O | Me | CHMe | 4-Cl |
| 745 | t-Bu | Cl | O | H | O | Me | CHMe | 4-Me |

TABLE 2-continued

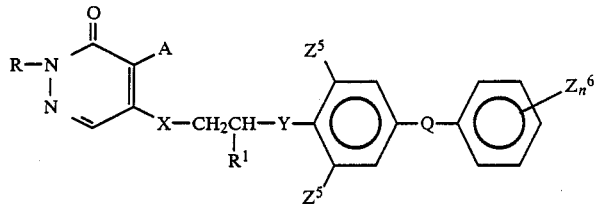

| No. | R | A | X | R¹ | Y | Z⁵ | Q | Z⁶$_n$ |
|---|---|---|---|---|---|---|---|---|
| 746 | t-Bu | Cl | O | H | O | Me | CHMe | 4-OMe |
| 747 | t-Bu | Cl | O | H | O | i-Pr | CHMe | H |
| 748 | t-Bu | Cl | O | H | O | i-Pr | CHMe | 4-Cl |
| 749 | t-Bu | Cl | O | H | O | i-Pr | CHMe | 4-Me |
| 750 | t-Bu | Cl | O | H | O | i-Pr | CHMe | 4-OMe |
| 763 | t-Bu | Cl | O | H | O | Cl | COCH₂ | H |
| 767 | t-Bu | Cl | O | H | O | Br | COCH₂ | H |
| 769 | t-Bu | Cl | O | H | O | Me | COCH₂ | H |
| 777 | t-Bu | Cl | O | H | O | Me | CH₂CH₂ | H |
| 781 | t-Bu | Cl | S | H | O | H | CHOH | H |
| 782 | t-Bu | Cl | S | H | O | H | CHOH | 4-Cl |
| 783 | t-Bu | Cl | S | H | O | Cl | CHOH | H |
| 784 | t-Bu | Cl | S | H | O | Cl | CHOH | 4-Cl |
| 785 | t-Bu | Cl | S | H | O | Me | CHOH | H |
| 786 | t-Bu | Cl | S | H | O | Me | CHOH | 4-Cl |
| 787 | t-Bu | Cl | S | H | O | Me | CHOH | 4-F |
| 788 | t-Bu | Cl | S | H | O | Me | CHOH | 4-Me |
| 789 | t-Bu | Cl | S | H | O | Me | CHOH | 2-Cl,4-Cl |
| 790 | t-Bu | Cl | S | H | O | Me | CHOH | 2-Me,4-Me |
| 791 | t-Bu | Cl | S | H | O | H | CHOMe | H |
| 792 | t-Bu | Cl | S | H | O | H | CHOMe | 4-Cl |
| 793 | t-Bu | Cl | S | H | O | Me | CHOMe | H |
| 794 | t-Bu | Cl | S | H | O | Me | CHOMe | 4-Cl |
| 795 | t-Bu | Cl | S | H | O | Me | CHOMe | 4-F |
| 796 | t-Bu | Cl | S | H | O | Me | CHOMe | 4-Me |
| 797 | t-Bu | Cl | S | H | O | Me | CHOMe | 2-Cl,4-Cl |
| 798 | t-Bu | Cl | S | H | O | Me | CHOMe | 2-Me,4-Me |
| 799 | t-Bu | Cl | S | H | O | Me | CHOEt | H |
| 800 | t-Bu | Cl | S | H | O | Me | CHOPr | H |
| 801 | t-Bu | Cl | S | H | O | H | C(OMe)₂ | H |
| 802 | t-Bu | Cl | S | H | O | H | C(OMe)₂ | 4-Cl |
| 803 | t-Bu | Cl | S | H | O | Cl | C(OMe)₂ | H |
| 804 | t-Bu | Cl | S | H | O | Cl | C(OMe)₂ | 4-Cl |
| 805 | t-Bu | Cl | S | H | O | Me | C(OMe)₂ | H |
| 806 | t-Bu | Cl | S | H | O | Me | C(OMe)₂ | 4-Cl |
| 807 | t-Bu | Cl | S | H | O | Me | C(OMe)₂ | 4-F |
| 808 | t-Bu | Cl | S | H | O | Me | C(OMe)₂ | 4-Me |
| 809 | t-Bu | Cl | S | H | O | Me | C(OMe)₂ | 2-Cl,4-Cl |
| 810 | t-Bu | Cl | S | H | O | Me | C(OMe)₂ | 2-Me,4-Me |
| 811 | t-Bu | Cl | S | H | O | H | CHCl | H |
| 812 | t-Bu | Cl | S | H | O | H | CHCl | 4-Cl |
| 813 | t-Bu | Cl | S | H | O | Cl | CHCl | H |
| 814 | t-Bu | Cl | S | H | O | Cl | CHCl | 4-Cl |
| 815 | t-Bu | Cl | S | H | O | Me | CHCl | H |
| 816 | t-Bu | Cl | S | H | O | Me | CHCl | 4-Cl |
| 817 | t-Bu | Cl | S | H | O | Me | CHCl | 4-F |
| 818 | t-Bu | Cl | S | H | O | Me | CHCl | 4-Me |
| 819 | t-Bu | Cl | S | H | O | Me | CHCl | 2-Cl,4-Cl |
| 820 | t-Bu | Cl | S | H | O | Me | CHCl | 2-Me,4-Me |

TABLE 3

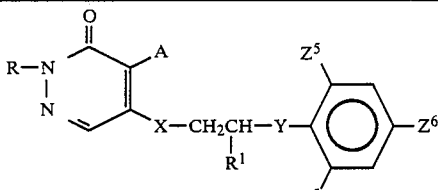

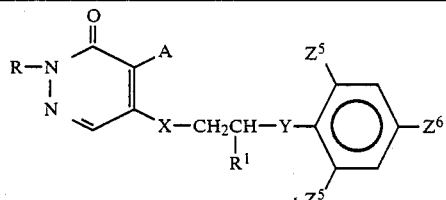

| No. | R | A | X | R¹ | Y | Z⁵ | Z⁶ |
|---|---|---|---|---|---|---|---|
| 841 | t-Bu | Cl | S | H | O | Me | CH₂OH |
| 842 | t-Bu | Cl | S | H | O | Me | CH(OH)CH₃ |
| 843 | t-Bu | Cl | S | H | O | Me | CH(OH)CH₂CH₃ |
| 844 | t-Bu | Cl | S | H | O | Me | CH(OH)CH₂CH₂CH₃ |
| 845 | t-Bu | Cl | S | H | O | Me | CH₂CH₂CH₂OH |
| 846 | t-Bu | Cl | S | H | O | Me | CH₂OCOCH₃ |
| 847 | t-Bu | Cl | S | H | O | Me | CH₂OCOEt |
| 848 | t-Bu | Cl | S | H | O | Me | CHMeOCOCH₃ |
| 849 | t-Bu | Cl | S | H | O | Me | CHEtOCOCH₃ |
| 850 | t-Bu | Cl | S | H | O | Me | CH₂OMe |
| 851 | t-Bu | Cl | S | H | O | Me | CH₂OEt |
| 852 | t-Bu | Cl | S | H | O | Me | CH₂OPr |

TABLE 3-continued

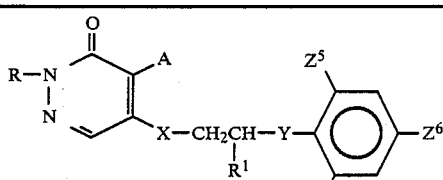

| No. | R | A | X | R¹ | Y | Z⁵ | Z⁶ |
|---|---|---|---|---|---|---|---|
| 853 | t-Bu | Cl | S | H | O | Me | CH₂O—i-Pr |
| 854 | t-Bu | Cl | S | H | O | Me | CHMeOMe |
| 855 | t-Bu | Cl | S | H | O | Me | CHMeOEt |
| 856 | t-Bu | Cl | S | H | O | Me | CHMeOPr |
| 857 | t-Bu | Cl | S | H | O | Me | CHEtOMe |
| 858 | t-Bu | Cl | S | H | O | Me | CHEtOEt |
| 859 | t-Bu | Cl | S | H | O | Me | C(OMe)₂CH₃ |
| 860 | t-Bu | Cl | S | H | O | Me | C(OEt)₂CH₃ |
| 861 | t-Bu | Cl | S | H | O | Me | C(OMe)₂CH₂CH₃ |
| 862 | t-Bu | Cl | S | H | O | Me | C(OEt)₂CH₂CH₃ |
| 863 | t-Bu | Cl | S | H | O | Me | CH₂SMe |
| 864 | t-Bu | Cl | S | H | O | Me | CH₂SEt |
| 865 | t-Bu | Cl | S | H | O | Me | CH₂SPr |
| 866 | t-Bu | Cl | S | H | O | Me | CH₂S-i-Pr |
| 867 | t-Bu | Cl | S | H | O | Me | CH₂SOMe |
| 868 | t-Bu | Cl | S | H | O | Me | CH₂SOEt |
| 869 | t-Bu | Cl | S | H | O | Me | CH₂SOPr |
| 870 | t-Bu | Cl | S | H | O | Me | CH₂SO—i-Pr |
| 871 | t-Bu | Cl | S | H | O | Me | CH₂SO₂Me |
| 872 | t-Bu | Cl | S | H | O | Me | CH₂SO₂Et |
| 873 | t-Bu | Cl | S | H | O | Me | CH₂SO₂Pr |
| 874 | t-Bu | Cl | S | H | O | Me | CH₂SO₂—i-Pr |
| 875 | t-Bu | Cl | S | H | O | Me | CH₂NMe₂ |
| 876 | t-Bu | Cl | S | H | O | Me | CH₂NEt₂ |
| 877 | t-Bu | Cl | S | H | O | Me | CH₂NPr₂ |
| 878 | t-Bu | Cl | S | H | O | Me | CH₂COCH₃ |
| 879 | t-Bu | Cl | S | H | O | Me | CH₂COEt |
| 880 | t-Bu | Cl | S | H | O | Me | CH₂COPr |
| 881 | t-Bu | Cl | S | H | O | Me | CH₂CH₂COCH₃ |
| 882 | t-Bu | Cl | S | H | O | Me | CH₂CH₂COEt |
| 883 | t-Bu | Cl | S | H | O | Me | CH₂CO₂Me |
| 884 | t-Bu | Cl | S | H | O | Me | CH₂CO₂Et |
| 885 | t-Bu | Cl | S | H | O | Me | CH₂CH₂CO₂Me |
| 886 | t-Bu | Cl | S | H | O | Me | CH₂CH₂CO₂Et |
| 887 | t-Bu | Cl | S | H | O | Me | CH₂CN |
| 888 | t-Bu | Cl | S | H | O | Me | CH₂CH₂CN |
| 889 | t-Bu | Cl | S | H | O | Me | CH₂CH₂CH₂CN |
| 890 | t-Bu | Cl | S | H | O | Me | CH₂CH₂CH₂CH₂CN |
| 891 | t-Bu | Cl | S | H | O | Me | CHCNCH₃ |
| 892 | t-Bu | Cl | S | H | O | Me | CHCNCH₂CH₃ |
| 893 | t-Bu | Cl | S | H | O | Me | CHCNCH₂CH₂CH₃ |
| 894 | t-Bu | Cl | S | H | O | Me | CH=NOMe |
| 895 | t-Bu | Cl | S | H | O | Me | CMe=NOMe |
| 896 | t-Bu | Cl | S | H | O | Me | CMe=NOEt |
| 897 | t-Bu | Cl | S | H | O | Me | CEt=NOMe |
| 898 | t-Bu | Cl | S | H | O | Me | CEt=NOEt |
| 899 | t-Bu | Cl | S | H | O | Cl | CH₂OMe |
| 900 | t-Bu | Cl | S | H | O | Cl | CH₂OEt |
| 901 | t-Bu | Cl | S | H | O | Me | OCH₂OMe |
| 902 | t-Bu | Cl | S | H | O | Me | OCH₂OEt |
| 903 | t-Bu | Cl | S | H | O | Me | OCH₂OPr |
| 904 | t-Bu | Cl | S | H | O | Me | OCH₂O—i-Pr |
| 905 | t-Bu | Cl | S | H | O | Me | OCH₂CH₂OMe |
| 906 | t-Bu | Cl | S | H | O | Me | OCH₂CH₂OEt |
| 907 | t-Bu | Cl | S | H | O | Me | OCH₂CH₂OPr |
| 908 | t-Bu | Cl | S | H | O | Me | OCH₂CH₂O—i-Pr |
| 909 | t-Bu | Cl | S | H | O | Me | OCH₂SMe |
| 910 | t-Bu | Cl | S | H | O | Me | OCH₂SEt |
| 911 | t-Bu | Cl | S | H | O | Me | OCH₂CH₂SMe |
| 912 | t-Bu | Cl | S | H | O | Me | OCH₂CH₂SEt |
| 913 | t-Bu | Cl | S | H | O | Me | OCH₂SOMe |
| 914 | t-Bu | Cl | S | H | O | Me | OCH₂SO₂Me |
| 915 | t-Bu | Cl | S | H | O | Me | OCH₂SOMe |
| 916 | t-Bu | Cl | S | H | O | Me | OCH₂CH₂SO₂Me |
| 917 | t-Bu | Cl | S | H | O | Me | OCH₂NMe₂ |
| 918 | t-Bu | Cl | S | H | O | Me | OCH₂CH₂NMe₂ |
| 919 | t-Bu | Cl | S | H | O | Me | OCH₂COCH₃ |
| 920 | t-Bu | Cl | S | H | O | Me | OCH₂COEt |
| 921 | t-Bu | Cl | S | H | O | Me | OCH₂CH₂COCH₃ |
| 922 | t-Bu | Cl | S | H | O | Me | OCH₂CH₂COEt |
| 923 | t-Bu | Cl | S | H | O | Me | OCH₂CO₂Me |

TABLE 3-continued

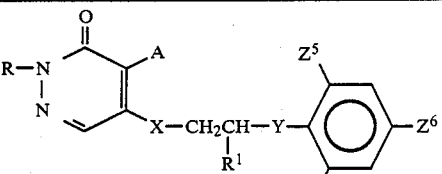

| No. | R | A | X | R¹ | Y | Z⁵ | Z⁶ |
|---|---|---|---|---|---|---|---|
| 924 | t-Bu | Cl | S | H | O | Me | OCH₂CO₂Et |
| 925 | t-Bu | Cl | S | H | O | Me | OCH₂CH₂CO₂Me |
| 926 | t-Bu | Cl | S | H | O | Me | OCH₂CH₂CO₂Et |
| 927 | t-Bu | Cl | S | H | O | Me | OCH₂CN |
| 928 | t-Bu | Cl | S | H | O | Me | OCH₂CH₂CN |
| 929 | t-Bu | Cl | S | H | O | H | OCH₂OMe |
| 930 | t-Bu | Cl | S | H | O | H | OCH₂OEt |
| 931 | t-Bu | Cl | S | H | O | Me | COCH₂F |
| 932 | t-Bu | Cl | S | H | O | Me | COCH₂Cl |
| 933 | t-Bu | Cl | S | H | O | Me | COCH₂Br |
| 934 | t-Bu | Cl | S | H | O | Me | COCF₃ |
| 935 | t-Bu | Cl | S | H | O | Me | COCHClCH₃ |
| 936 | t-Bu | Cl | S | H | O | Me | COCHBrCH₃ |
| 937 | t-Bu | Cl | S | H | O | Me | COCH₂CF₃ |
| 938 | t-Bu | Cl | S | H | O | Me | COCH₂CH₂F |
| 939 | t-Bu | Cl | S | H | O | Me | COCH₂CH₂Cl |
| 940 | t-Bu | Cl | S | H | O | Me | COCH₂CH₂Br |
| 941 | t-Bu | Cl | S | H | O | Me | COCH₂OMe |
| 942 | t-Bu | Cl | S | H | O | Me | COCH₂OEt |
| 943 | t-Bu | Cl | S | H | O | Me | COCH₂OPr |
| 944 | t-Bu | Cl | S | H | O | Me | COCHMeOMe |
| 945 | t-Bu | Cl | S | H | O | Me | COCHMeOEt |
| 946 | t-Bu | Cl | S | H | O | Me | COCH₂CH₂OMe |
| 947 | t-Bu | Cl | S | H | O | Me | COCH₂CH₂OEt |
| 948 | t-Bu | Cl | S | H | O | Me | COCH₂SMe |
| 949 | t-Bu | Cl | S | H | O | Me | COCH₂SEt |
| 950 | t-Bu | Cl | S | H | O | Me | COCH₂SPr |
| 951 | t-Bu | Cl | S | H | O | Me | COCHMeSMe |
| 952 | t-Bu | Cl | S | H | O | Me | COCHMeSEt |
| 953 | t-Bu | Cl | S | H | O | Me | COCH₂CH₂SMe |
| 954 | t-Bu | Cl | S | H | O | Me | COCH₂CH₂SEt |
| 955 | t-Bu | Cl | S | H | O | Me | COCH₂SOMe |
| 956 | t-Bu | Cl | S | H | O | Me | COCH₂SOEt |
| 957 | t-Bu | Cl | S | H | O | Me | COCH₂CH₂SOMe |
| 958 | t-Bu | Cl | S | H | O | Me | COCH₂SO₂Me |
| 959 | t-Bu | Cl | S | H | O | Me | COCH₂SO₂Et |
| 960 | t-Bu | Cl | S | H | O | Me | COCH₂CH₂SO₂Me |
| 961 | t-Bu | Cl | S | H | O | Me | COCH₂NMe₂ |
| 962 | t-Bu | Cl | S | H | O | Me | COCH₂NEt₂ |
| 963 | t-Bu | Cl | S | H | O | Me | COCH₂CH₂NMe₂ |
| 964 | t-Bu | Cl | S | H | O | Me | COCH₂CH₂NEt₂ |
| 965 | t-Bu | Cl | S | H | O | Me | COCH₂COCH₃ |
| 966 | t-Bu | Cl | S | H | O | Me | COCH₂CO₂Me |
| 967 | t-Bu | Cl | S | H | O | Me | COCH₂CO₂Et |
| 968 | t-Bu | Cl | S | H | O | Me | COCH₂CH₂CO₂Me |
| 969 | t-Bu | Cl | S | H | O | Me | COCH₂CH₂CO₂Et |
| 970 | t-Bu | Cl | S | H | O | Me | COCH₂CN |
| 971 | t-Bu | Cl | S | H | O | Me | COCH₂CH₂CN |
| 972 | t-Bu | Cl | S | H | O | Me | COCHMeCN |
| 973 | t-Bu | Cl | S | H | O | H | COCH₂Cl |
| 974 | t-Bu | Cl | S | H | O | H | COCH₂Br |
| 975 | t-Bu | Cl | S | H | O | H | COCH₂F |
| 976 | t-Bu | Cl | S | H | O | H | COCH₂CH₂Cl |
| 977 | t-Bu | Cl | S | H | O | H | COCH₂CH₂F |
| 978 | t-Bu | Cl | S | H | O | H | COCH₂OMe |
| 979 | t-Bu | Cl | S | H | O | H | COCH₂OEt |
| 980 | t-Bu | Cl | S | H | O | H | COCH₂OPr |
| 981 | t-Bu | Cl | S | H | O | H | COCH₂SMe |
| 982 | t-Bu | Cl | S | H | O | Cl | COCH₂Cl |
| 983 | t-Bu | Cl | S | H | O | Cl | COCH₂Br |
| 984 | t-Bu | Cl | S | H | O | Cl | COCH₂F |
| 985 | t-Bu | Cl | S | H | O | Cl | COCH₂CH₂Cl |
| 986 | t-Bu | Cl | S | H | O | Cl | COCH₂CH₂F |
| 987 | t-Bu | Cl | S | H | O | Cl | COCH₂OMe |
| 988 | t-Bu | Cl | S | H | O | Cl | COCH₂OEt |
| 989 | t-Bu | Cl | S | H | O | Cl | COCH₂OPr |
| 990 | t-Bu | Cl | S | H | O | Cl | COCH₂SMe |
| 991 | t-Bu | Cl | O | H | O | Me | CH₂OH |
| 992 | t-Bu | Cl | O | H | O | Me | CH(OH)CH₃ |
| 993 | t-Bu | Cl | O | H | O | Me | CH(OH)CH₂CH₃ |
| 994 | t-Bu | Cl | O | H | O | Me | CH(OH)CH₂CH₂CH₃ |

TABLE 3-continued

| No. | R | A | X | R¹ | Y | Z⁵ | Z⁶ |
|---|---|---|---|---|---|---|---|
| 995 | t-Bu | Cl | O | H | O | Me | CH₂CH₂CH₂OH |
| 996 | t-Bu | Cl | O | H | O | Me | CH₂OCOCH₃ |
| 997 | t-Bu | Cl | O | H | O | Me | CH₂OCOEt |
| 998 | t-Bu | Cl | O | H | O | Me | CHMeOCOCH₃ |
| 999 | t-Bu | Cl | O | H | O | Me | CHEtOCOCH₃ |
| 1000 | t-Bu | Cl | O | H | O | Me | CH₂OMe |
| 1001 | t-Bu | Cl | O | H | O | Me | CH₂OEt |
| 1002 | t-Bu | Cl | O | H | O | Me | CH₂OPr |
| 1003 | t-Bu | Cl | O | H | O | Me | CH₂O—i-Pr |
| 1004 | t-Bu | Cl | O | H | O | Me | CHMeOMe |
| 1005 | t-Bu | Cl | O | H | O | Me | CHMeOEt |
| 1006 | t-Bu | Cl | O | H | O | Me | CHMeOPr |
| 1007 | t-Bu | Cl | O | H | O | Me | CHEtOMe |
| 1008 | t-Bu | Cl | O | H | O | Me | CHEtOEt |
| 1009 | t-Bu | Cl | O | H | O | Me | C(OMe)₂CH₃ |
| 1010 | t-Bu | Cl | O | H | O | Me | C(OEt)₂CH₃ |
| 1011 | t-Bu | Cl | O | H | O | Me | C(OMe)₂CH₂CH₃ |
| 1012 | t-Bu | Cl | O | H | O | Me | C(OEt)₂CH₂CH₃ |
| 1013 | t-Bu | Cl | O | H | O | Me | CH₂SMe |
| 1014 | t-Bu | Cl | O | H | O | Me | CH₂SEt |
| 1015 | t-Bu | Cl | O | H | O | Me | CH₂SPr |
| 1016 | t-Bu | Cl | O | H | O | Me | CH₂S-i-Pr |
| 1017 | t-Bu | Cl | O | H | O | Me | CH₂SOMe |
| 1018 | t-Bu | Cl | O | H | O | Me | CH₂SOEt |
| 1019 | t-Bu | Cl | O | H | O | Me | CH₂SOPr |
| 1020 | t-Bu | Cl | O | H | O | Me | CH₂SO—i-Pr |
| 1021 | t-Bu | Cl | O | H | O | Me | CH₂SO₂Me |
| 1022 | t-Bu | Cl | O | H | O | Me | CH₂SO₂Et |
| 1023 | t-Bu | Cl | O | H | O | Me | CH₂SO₂Pr |
| 1024 | t-Bu | Cl | O | H | O | Me | CH₂SO₂—i-Pr |
| 1025 | t-Bu | Cl | O | H | O | Me | CH₂NMe₂ |
| 1026 | t-Bu | Cl | O | H | O | Me | CH₂NEt₂ |
| 1027 | t-Bu | Cl | O | H | O | Me | CH₂NPr₂ |
| 1028 | t-Bu | Cl | O | H | O | Me | CH₂COCH₃ |
| 1029 | t-Bu | Cl | O | H | O | Me | CH₂COEt |
| 1030 | t-Bu | Cl | O | H | O | Me | CH₂COPr |
| 1031 | t-Bu | Cl | O | H | O | Me | CH₂CH₂COCH₃ |
| 1032 | t-Bu | Cl | O | H | O | Me | CH₂CH₂COEt |
| 1033 | t-Bu | Cl | O | H | O | Me | CH₂CO₂Me |
| 1034 | t-Bu | Cl | O | H | O | Me | CH₂SO₂Et |
| 1035 | t-Bu | Cl | O | H | O | Me | CH₂CH₂CO₂Me |
| 1036 | t-Bu | Cl | O | H | O | Me | CH₂CH₂CO₂Et |
| 1037 | t-Bu | Cl | O | H | O | Me | CH₂CN |
| 1038 | t-Bu | Cl | O | H | O | Me | CH₂CH₂CN |
| 1039 | t-Bu | Cl | O | H | O | Me | CH₂CH₂CH₂CN |
| 1040 | t-Bu | Cl | O | H | O | Me | CH₂CH₂CH₂CH₂CN |
| 1041 | t-Bu | Cl | O | H | O | Me | CHCNCH₃ |
| 1042 | t-Bu | Cl | O | H | O | Me | CHCNCH₂CH₃ |
| 1043 | t-Bu | Cl | O | H | O | Me | CHCNCH₂CH₂CH₃ |
| 1044 | t-Bu | Cl | O | H | O | Me | CH=NOMe |
| 1045 | t-Bu | Cl | O | H | O | Me | CMe=NOMe |
| 1046 | t-Bu | Cl | O | H | O | Me | CMe=NOEt |
| 1047 | t-Bu | Cl | O | H | O | Me | CEt=NOMe |
| 1048 | t-Bu | Cl | O | H | O | Me | CEt=NOEt |
| 1049 | t-Bu | Cl | O | H | O | Cl | CH₂OMe |
| 1050 | t-Bu | Cl | O | H | O | Cl | CH₂OEt |
| 1051 | t-Bu | Cl | O | H | O | Me | OCH₂OMe |
| 1052 | t-Bu | Cl | O | H | O | Me | OCH₂OEt |
| 1053 | t-Bu | Cl | O | H | O | Me | OCH₂OPr |
| 1054 | t-Bu | Cl | O | H | O | Me | OCH₂O—i-Pr |
| 1055 | t-Bu | Cl | O | H | O | Me | OCH₂CH₂OMe |
| 1056 | t-Bu | Cl | O | H | O | Me | OCH₂CH₂OEt |
| 1057 | t-Bu | Cl | O | H | O | Me | OCH₂CH₂OPr |
| 1058 | t-Bu | Cl | O | H | O | Me | OCH₂CH₂O—i-Pr |
| 1059 | t-Bu | Cl | O | H | O | Me | OCH₂SMe |
| 1060 | t-Bu | Cl | O | H | O | Me | OCH₂SEt |
| 1061 | t-Bu | Cl | O | H | O | Me | OCH₂CH₂SMe |
| 1062 | t-Bu | Cl | O | H | O | Me | OCH₂CH₂SEt |
| 1063 | t-Bu | Cl | O | H | O | Me | OCH₂SOMe |
| 1064 | t-Bu | Cl | O | H | O | Me | OCH₂SO₂Me |
| 1065 | t-Bu | Cl | O | H | O | Me | OCH₂CH₂SOMe |
| 1066 | t-Bu | Cl | O | H | O | Me | OCH₂CH₂SO₂Me |
| 1067 | t-Bu | Cl | O | H | O | Me | OCH₂NMe₂ |
| 1068 | t-Bu | Cl | O | H | O | Me | OCH₂CH₂NMe₂ |
| 1069 | t-Bu | Cl | O | H | O | Me | OCH₂COCH₃ |
| 1070 | t-Bu | Cl | O | H | O | Me | OCH₂COEt |
| 1071 | t-Bu | Cl | O | H | O | Me | OCH₂CH₂COCH₃ |
| 1072 | t-Bu | Cl | O | H | O | Me | OCH₂CH₂COEt |
| 1073 | t-Bu | Cl | O | H | O | Me | OCH₂CO₂Me |
| 1074 | t-Bu | Cl | O | H | O | Me | OCH₂CO₂Et |
| 1075 | t-Bu | Cl | O | H | O | Me | OCH₂CH₂CO₂Me |
| 1076 | t-Bu | Cl | O | H | O | Me | OCH₂CH₂CO₂Et |
| 1077 | t-Bu | Cl | O | H | O | Me | OCH₂CN |
| 1078 | t-Bu | Cl | O | H | O | Me | OCH₂CH₂CN |
| 1081 | t-Bu | Cl | O | H | O | Me | COCH₂F |
| 1082 | t-Bu | Cl | O | H | O | Me | COCH₂Cl |
| 1083 | t-Bu | Cl | O | H | O | Me | COCH₂Br |
| 1084 | t-Bu | Cl | O | H | O | Me | COCF₃ |
| 1085 | t-Bu | Cl | O | H | O | Me | COCHClCH₃ |
| 1086 | t-Bu | Cl | O | H | O | Me | COCHBrCH₃ |
| 1087 | t-Bu | Cl | O | H | O | Me | COCH₂CF₃ |
| 1088 | t-Bu | Cl | O | H | O | Me | COCH₂CH₂F |
| 1089 | t-Bu | Cl | O | H | O | Me | COCH₂CH₂Cl |
| 1090 | t-Bu | Cl | O | H | O | Me | COCH₂CH₂Br |
| 1091 | t-Bu | Cl | O | H | O | Me | COCH₂OMe |
| 1092 | t-Bu | Cl | O | H | O | Me | COCH₂OEt |
| 1093 | t-Bu | Cl | O | H | O | Me | COCH₂OPr |
| 1094 | t-Bu | Cl | O | H | O | Me | COCHMeOMe |
| 1095 | t-Bu | Cl | O | H | O | Me | COCHMeOEt |
| 1096 | t-Bu | Cl | O | H | O | Me | COCH₂CH₂OMe |
| 1097 | t-Bu | Cl | O | H | O | Me | COCH₂CH₂OEt |
| 1098 | t-Bu | Cl | O | H | O | Me | COCH₂SMe |
| 1099 | t-Bu | Cl | O | H | O | Me | COCH₂SEt |
| 1100 | t-Bu | Cl | O | H | O | Me | COCH₂SPr |
| 1101 | t-Bu | Cl | O | H | O | Me | COCHMeSMe |
| 1102 | t-Bu | Cl | O | H | O | Me | COCHMeSEt |
| 1103 | t-Bu | Cl | O | H | O | Me | COCH₂CH₂SMe |
| 1104 | t-Bu | Cl | O | H | O | Me | COCH₂CH₂SEt |
| 1105 | t-Bu | Cl | O | H | O | Me | COCH₂SOMe |
| 1106 | t-Bu | Cl | O | H | O | Me | COCH₂SOEt |
| 1107 | t-Bu | Cl | O | H | O | Me | COCH₂CH₂SOMe |
| 1108 | t-Bu | Cl | O | H | O | Me | COCH₂SO₂Me |
| 1109 | t-Bu | Cl | O | H | O | Me | COCH₂SO₂Et |
| 1110 | t-Bu | Cl | O | H | O | Me | COCH₂CH₂SO₂Me |
| 1111 | t-Bu | Cl | O | H | O | Me | COCH₂NMe₂ |
| 1112 | t-Bu | Cl | O | H | O | Me | COCH₂NEt₂ |
| 1113 | t-Bu | Cl | O | H | O | Me | COCH₂CH₂NMe₂ |
| 1114 | t-Bu | Cl | O | H | O | Me | COCH₂CH₂NEt₂ |
| 1115 | t-Bu | Cl | O | H | O | Me | COCH₂COCH₃ |
| 1116 | t-Bu | Cl | O | H | O | Me | COCH₂CO₂Me |
| 1117 | t-Bu | Cl | O | H | O | Me | COCH₂CO₂Et |
| 1118 | t-Bu | Cl | O | H | O | Me | COCH₂CH₂CO₂Me |
| 1119 | t-Bu | Cl | O | H | O | Me | COCH₂CH₂CO₂Et |
| 1120 | t-Bu | Cl | O | H | O | Me | COCH₂CN |
| 1121 | t-Bu | Cl | O | H | O | Me | COCH₂CH₂CN |
| 1122 | t-Bu | Cl | O | H | O | Me | COCHMeCN |
| 1132 | t-Bu | Cl | O | H | O | Cl | COCH₂Cl |
| 1133 | t-Bu | Cl | O | H | O | Cl | COCH₂Br |
| 1134 | t-Bu | Cl | O | H | O | Cl | COCH₂F |
| 1135 | t-Bu | Cl | O | H | O | Cl | COCH₂CH₂Cl |
| 1136 | t-Bu | Cl | O | H | O | Cl | COCH₂CH₂F |
| 1137 | t-Bu | Cl | O | H | O | Cl | COCH₂OMe |
| 1138 | t-Bu | Cl | O | H | O | Cl | COCH₂OEt |
| 1139 | t-Bu | Cl | O | H | O | Cl | COCH₂OPr |
| 1140 | t-Bu | Cl | O | H | O | Cl | COCH₂SMe |
| 1141 | t-Bu | Cl | S | H | O | Me | NHSO₂Me |
| 1142 | t-Bu | Cl | S | H | O | Me | NHCONMe₂ |
| 1143 | t-Bu | Cl | S | H | O | Me | C(Me)=NNMe₂ |

Preferred compounds according to the present invention include:

2-t-butyl-4-chloro-5-[2-2,6-dimethyl-4-(4-methylphenoxy)phenoxy ethylthio]-3(2H)-pyridazinone of claim 1 having the formula:

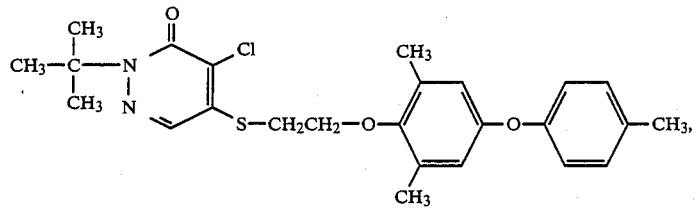

2-t-butyl-4-chloro-5-[2-(2,6-dimethyl-4-phenoxyphenoxy)ethylthio]-3(2H)-pyridazinone of claim 1 having the formula:

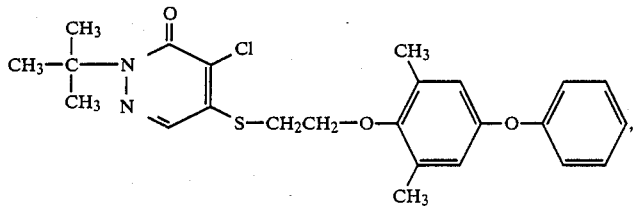

2-t-butyl-4-chloro-5-[2-{2,6-dimethyl-4-(2,4-difluorobenzoyl)phenoxy}ethylthio]-3(2H)-pyridazinone of claim 1 having the formula:

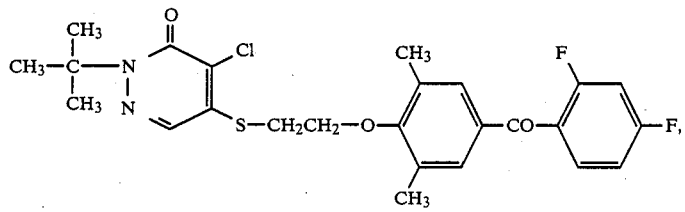

2-t-butyl-4-chloro-5-[2-(2,6-dimethyl-4-ethoxyphenoxy)ethylthio]-3(2H)-pyridazinone of claim 1 having the formula:

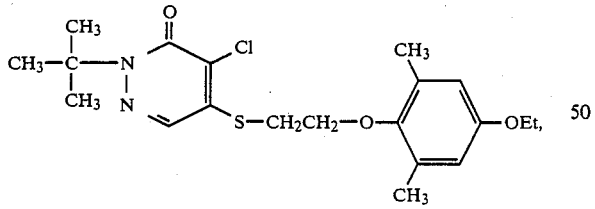

2-t-butyl-4-chloro-5-[2-(2,6-dimethyl-4-methoxymethylphenoxy)ethylthio]-3(2H)-pyridazinone of claim 1 having the formula:

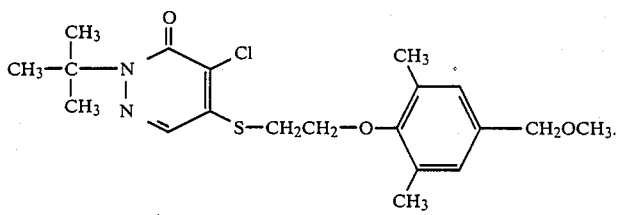

The compound numbers in Tables 1 to 3 are referred to in preparation examples, formulation examples and test examples, which will be mentioned below.

The compounds of the present invention can be prepared by reacting a compound of the general formula (II):

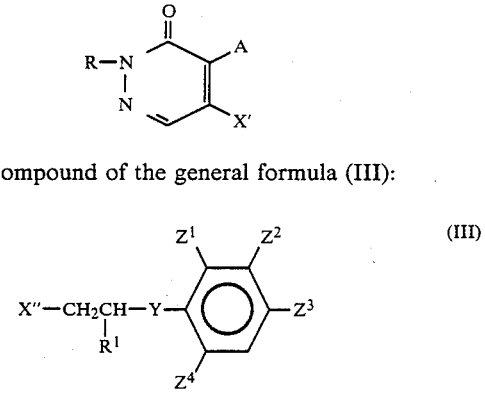

with a compound of the general formula (III):

(III)

$$X''-CH_2CH(R^1)-Y-\text{(aryl with } Z^1, Z^2, Z^3, Z^4\text{)}$$

wherein R, A, $R^1$, Y, and $Z^1$–$Z^4$ have the same meanings as defined above, and X' and X'' represent halogen atom, —SM or —OM in which M means hydrogen atom or alkali metal atom.

In general, it is preferable to use —SM or —OM as X″ in the general formula (III) when X′ in the general formula (II) is halogen atom, and to use halogen atom as X″ in the general formula (III) when X′ in the general formula (II) is —SM or —OM (wherein M represents hydrogen atom or alkali metal atom), with the proviso that when X′ is halogen atom, X″ represents —Sm or —OM, and when X′ is —SM or —OM, X″ represents halogen atom.

It is also preferable to prepare the compounds of the present invention in the presence of appropriate bases and in solvents which do not affect the reaction. When M is alkali metal atom, the presence of the base is not necessarily needed.

As the solvents in the present invention can be used lower alcohols such as methanol, ethanol, etc.; ketones such as acetone, methylethylketone, etc.; hydrocarbons such as benzene, toluene, etc.; ethers such as isopropylether, tetrahydrofuran, 1,4-dioxane, etc.; amides such as N,N-dimethylformamide, hexamethyl phosphoric triamides, etc.; halogenated hydrocarbons such as dichloromethane, dichloroethane, etc. As necessary, mixtures of these solvens or mixtures of these solvents and water can also be used.

Inorganic bases such as sodium hydride, sodium hydroxide, potassium hydroxide, sodium carbonate, potassium carbonate, sodium hydrogen-carbonate, etc., and organic bases such as sodium methoxide, sodium ethoxide, triethylamine, pyridine, etc. can be used as the base. If necessary, tetraammonium salts, for example, triethylbenzylammonium chloride, etc., may be added to the reaction system as catalyst.

The reaction temperature may be in a range of from −20° C. to the boiling point of the solvent to be used in the reaction. The reaction temperature is preferably in a range of from −5° C. to the boiling point of the solvent to be used in the reaction.

The ratio of the raw material can be optionally selected, but it is advantageous to conduct the reaction using equimolar or nearly equimolar amount of the materials.

Preparation of compounds of the present invention is described in more detail by the way of the following examples which are not to restrict to the invention.

PREPARATION EXAMPLE 1

Preparation of 2-t-butyl-4-chloro-5-(2′-[2″,6″-dimethylphenoxy)ethylthio]-3-(2H)-pyridazinone (Compound No. 24)

In 30 mm of N,N-dimethylformamide was dissolved 2.2 g of 2-t-butyl-4-chloro-5-mercapto-3(2H)-pyridazinone and 2.3 g of 2-(2′,6′-dimethylphenoxy)ethyl bromide, and thereto were added 1.1 g of anhydrous sodium carbonate. The resulting solution was stirred at room temperature for fifteen hours. This solution was poured into water and extracted with diethyl ether. The organic layer was dried over anhydrous sodium sulfate and freed of solvent under reduced pressure to give crystals. The crystals thus obtained were washed with n-hexane to give 3.5 g of the intended compound. m.p. 104.3°~105.2° C.

PREPARATION EXAMPLE 2

Preparation of 2-t-butyl-4-chloro-5-(2′-[2″,6″-dimethyl-4″-butylcarbonylphenoxy)ethylthio]-3-(2H)-pyridazinone (Compound No. 78)

In 30 mm of N,N-dimethylformamide was dissolved 2.2 g of 2-t-butyl-4-chloro-5-mercapto-3(2H)-pyridazinone and 3.0 g of 2-(2′,6′-dimethyl-4′butylcarbonylphenoxyethyl bromide and thereto were added 1.5 g of anhydrous sodium carbonate. The resulting solution was stirred at room temperature for fifteen hours. This solution was poured into water and extracted with diethyl ether. The organic layer was dried over anhydrous sodium sulfate and freed of solvent under reduced pressure to give a crude product. The crude product thus obtained was purified by means of column chromatography (on silica gel, eluting with benzene) to give 3.3 g of the intended compound as an oil.

PREPARATION EXAMPLE 3

Preparation of 2-t-butyl-4-chloro-5-[2′-(2″,6″-dimethyl-4″-benzoylphenoxy)ethylthio]-3-(2H)-pyridazinone (Compound No. 465)

In 50 ml of N,N-dimethylformamide were dissolved 6.6 g of 2-t-butyl-4-chloro-5-mercapto-3(2H)-pyridazinone and 10 g of 2-(2′,6′-dimethyl-4′-benzoylphenoxy)ethyl bromide, and thereto was added 5 g of anhydrous sodium carbonate. The solution was stirred at room temperature for seventeen hours. The resulting solution was poured into water and extracted with diethyl ether. The organic layer was dried over anhydrous sodium sulfate and freed of solvent by distillation under reduced pressure to give a crude product. The crude product thus obtained was purified by means of column chromatography (on silica gel, eluting with benzene) and crystallization (from 50 ml of n-hexanediethyl ether (4:1)) to give 13.3 g of the intended compound. m.p. 94.6°~96.2° C.

PREPARATION EXAMPLE 4

Preparation of 2-t-butyl-4-chloro-5-[2{-2,6-dimethyl-4-(4-methylphenoxy)phenoxy}ethylthio]-3(2H)-pyridazinone (Compound No. 429).

In 10 ml of N,N-dimethylformamide were dissolved 1.5 g of 2-t-butyl-4-chloro-5-mercapt-3(2H)-pyridazinone and 2.3 g of 2-{2,6-dimethyl-4-(4-methylphenoxy)-phenoxy}ethylbromide, and thereto was added 1.0 g of anhydrous sodium carbonate. The mixture was stirred for 15 hours at room temperature. The resulting solution was poured into water (50 ml) and then extracted with 50 ml of diethyl ether and further with 50 ml of ethyl acetate. The organic layer was washed with water, dried over anhydrous sodium sulfate and freed of solvent by distillation under reduced pressure to give 3.2 g of a crude product. The crude product was recrystallized from benzenehexane (1:3)(20 ml) to obtain 2.5 g of the intended compound. m.p.: 137.7°–140.7° C.

The physical properties of the compounds prepared according to one of the methods of the Preparation Examples 1 to 4 are shown in the following Table 4.

TABLE 4

| No. | m.p. (°C.) | No. | m.p. (°C.) |
|---|---|---|---|
| 12 | 109.2–111.6 | 56 | 86.4–91.5 |
| 13 | oil | 61 | 109.7–112.0 |
| 14 | oil | 70 | oil |
| 15 | oil | 71 | 152.9–153.7 |
| 16 | 61.0–63.0 | 72 | 116.9–118.2 |
| 17 | 65.0–70.0 | 73 | 106.9–108.6 |
| 18 | oil | 74 | 127.9–130.1 |
| 19 | oil | 75 | 126.1–129.2 |
| 21 | 87.0–88.5 | 76 | oil |
| 22 | 96.8–98.5 | 77 | 152.7–156.4 |
| 23 | 112.4–113.3 | 78 | oil |
| 24 | 104.3–105.2 | 79 | oil |
| 25 | oil | 80 | oil |
| 26 | 78.3–80.7 | 82 | 107.0–108.8 |
| 27 | 98.6–102.1 | 84 | 79.7–80.8 |
| 28 | oil | 85 | 90.0–91.5 |
| 29 | oil | 87 | oil |
| 30 | oil | 88 | 103.5–104.8 |
| 31 | 95.7–98.0 | 89 | 119.8–124.5 |
| 32 | 109.0–111.2 | 90 | oil |
| 33 | 106.6–109.2 | 92 | 117.2–120.1 |
| 34 | 95.4–97.0 | 93 | oil |
| 36 | oil | 94 | 108.2–109.2 |
| 38 | 123.4–127.3 | 95 | oil |
| 40 | 94.0–96.0 | 97 | oil |
| 41 | oil | 98 | oil |
| 44 | oil | 99 | oil |
| 45 | oil | 112 | 107.7–108.3 |
| 46 | 115.0–118.1 | 113 | 86.2–88.5 |
| 49 | oil | 148 | oil |
| 53 | oil | 150 | oil |
| 55 | 92.8–93.6 | 151 | 88.0–89.0 |
|  |  | 161 | 55.0–60.0 |
|  |  | 270 | 156.0–160.5 |
| 174 | oil | 271 | 116.1–117.6 |
| 202 | 85.0–87.0 | 272 | 159.9–161.3 |
| 219 | 126.5–127.7 | 273 | 122.0–124.8 |
| 223 | 111.1–113.5 | 275 | 98.1–104.2 |
| 224 | 97.0–101.0 | 277 | 143.1–145.6 |
| 225 | oil | 279 | 107.6–109.5 |
| 226 | 124.6–129.5 | 280 | 102.8–106.5 |
| 227 | 135.6–139.2 | 283 | 86.7–88.1 |
| 228 | 131.1–132.6 | 284 | 108.8–110.5 |
| 229 | 133.2–134.7 | 285 | 94.5–100.0 |
| 230 | 120.0–124.0 | 287 | 173.3–176.3 |
| 232 | 79.0–80.3 | 288 | 86.6–87.9 |
| 233 | 142.5–146.5 | 289 | 147.1–148.3 |
| 235 | 85.0–87.0 | 290 | 73.1–75.5 |
| 236 | 96.0–98.0 | 292 | oil |
| 239 | 155.7–157.4 | 293 | 64.1–64.2 |
| 240 | oil | 294 | 103.4–104.4 |
| 241 | 108.2–111.8 | 343 | 96.1–97.3 |
| 248 | 149.5–151.2 | 344 | 117.9–120.9 |
| 250 | 137.9–139.2 | 360 | oil |
| 251 | 88.0–93.0 | 421 | 120.3–128.2 |
| 256 | 130.6–134.1 | 463 | 150.2–151.8 |
| 265 | 112.9–114.5 | 465 | 94.6–96.2 |
| 266 | 171.0–173.8 | 466 | 156.9–158.1 |
| 267 | 150.6–152.9 | 467 | oil |
| 268 | 131.5–133.5 | 468 | 142.2–144.1 |
| 269 | 135.2–137.8 | 470 | oil |
| 472 | 153.1–154.5 | 656 | 113.0–116.0 |
| 474 | 129.2–131.4 | 660 | 143.9–145.6 |
| 475 | oil | 662 | 193.0–196.0 |
| 476 | oil | 664 | 168.6–170.9 |
| 480 | 138.0–140.0 | 670 | 153.0–154.3 |
| 482 | 162.0–164.6 | 672 | 143.0–144.8 |
| 484 | 125.1–126.4 | 673 | 177.5–179.0 |
| 490 | 108.9–111.2 | 676 | 122.7–123.4 |
| 492 | 126.5–128.0 | 678 | 157.6–159.1 |
| 493 | 158.7–161.3 | 680 | 137.1–138.1 |
| 494 | 134.4–135.4 | 694 | 139.2–140.4 |
| 496 | 121.7–122.5 | 697 | 163.4–165.0 |
| 498 | 113.8–115.9 | 698 | 179.8–182.2 |
| 500 | 135.3–137.3 | 699 | 116.7–117.7 |
| 514 | oil | 722 | 58.0–62.0 |
| 517 | 123.1–126.1 | 725 | 130.0–131.0 |
| 518 | 136.4–137.5 | 111 | 91.1–92.1 |
| 519 | 98.3–99.2 | 491 | 212.6–213.6 |
| 520 | oil | 477 | 116.6–118.6 |
| 527 | 105.9–107.6 | 306 | 125.9–127.6 |
| 542 | 115.2–116.4 | 671 | 224.5–226.5 |
| 545 | 130.7–132.5 | 657 | 137.6–139.1 |
| 643 | 156.8–158.0 | 152 | 98.9–101.5 |
| 646 | 202.3–204.0 | 489 | 161.0–163.6 |
| 647 | 135.8–137.8 | 83 | 121.0–122.0 |
| 652 | 163.9–166.0 | 278 | 142.7–144.7 |
| 654 | 168.9–170.1 | 153 | 87.5–90.0 |
| 655 | 134.1–135.9 |  |  |
| 198 | 93.3–94.8 | 609 | 153.1–157.0 |
| 100 | 104.7–106.7 | 610 | 134.0–136.0 |
| 102 | 135.4–136.5 | 612 | 180.0–183.0 |
| 127 | 119.0–120.6 | 618 | 1269–128.9 |
| 128 | 93.2–95.2 | 661 | 165.0–167.0 |
| 129 | 74.8–76.5 | 668 | 145.8–146.7 |
| 131 | 118.5–121.3 | 702 | 57.0–60.0 |
| 134 | 141.9–142.7 | 704 | 98.8–101.1 |
| 135 | 125.3–127.4 | 708 | 143.7–145.3 |
| 199 | 70.4–71.2 | 720 | 118.5–120.1 |
| 296 | 166.8–167.8 | 843 | 147.8–150.4 |
| 323 | 105.0–107.2 | 850 | 67.0–70.0 |
| 324 | 81.1–83.6 | 851 | oil |
| 426 | 119.3–120.4 | 852 | oil |
| 427 | 102.2–102.9 | 857 | oil |
| 429 | 137.7–140.7 | 863 | oil |
| 430 | 95.3–98.0 | 895 | 106.7–109.2 |
| 432 | 112.8–113.4 | 1000 | 105.0–107.0 |
| 438 | 102.2–102.9 | 1001 | 103.7–105.7 |
| 443 | 120.0–123.2 | 1002 | 94.3–96.7 |
| 481 | 142.4–143.5 | 1045 | 141.5–143.1 |
| 488 | 123.8–124.9 | 1141 | 216.0–218.0 |
| 522 | oil | 1142 | 173.6–175.8 |
| 524 | oil | 1143 | 121.4–124.1 |
| 528 | 103.4–104.5 | 589 | oil |
| 540 | 93.0–94.1 | 597 | oil |
| 606 | 167.5–170.3 | 777 | 101.5–105.6 |

When the compounds according to the present invention are used for insecticidal, acaricidal and/or nematicidal agents for agricultural and horticultural uses or for expellents of ticks parasitic on animals, they are generally mixed with appropriate carriers, for instance, solid carriers such as clay, talc, bentonite or diatomaceous earth, or liquid carriers such as water, alcohols (e.g., methanol and ethanol), aromatic hydrocarbons (e.g., benzene, toluene and xylene), chlorinated hydrocarbons, ethers, ketones, acid amides (e.g., dimethylformamide (DMF)) or esters (e.g., ethyl acetate). If desired, to these mixtures can be added a surfactant, eumulsifier, dispersing agent, suspending agent, penetrating agent, spreader, stabilizer and the like to put them into practical uses in the form of liquid preparation, smulsifiable concentration, wettable powder, dust, granule, flowable or the like. Moreover, the resulting mixtures may be incorporated with other herbicides, various insecticides, plant-growth regulating agents and/or synergists during preparation or application thereof, as necessary.

When the present compounds are used in the agricultural and horticultural fields, the amount to be applied as an active ingredient is in the range of 0.005 to 50 kg per hectare. It is more preferable to apply 0.01 to 5 kg/hectare.

When the present compounds are used for controlling ectoparasites on animals, in general, diluted aqueous solution of 2 to 50,000 ppm can be used as concentration of active ingredient, more preferably 10 to 1,000 ppm.

In the following, there are shown component ratios of formulations and formulation examples of insecticidal, acaricidal and/or nematicidal compositions and expellent compositions for ticks parasitic on animals, said compositions containing the compounds of the present invention as active ingredients. These examples are merely illustrative and not to restrict the invention. In the following examples, "part" means "part by weight" and "%" means "% by weight".

1. Components Ratio of Formulation (1) Emulsifiable concentrates

| Active ingredient: | 5–25% | |
|---|---|---|
| liquid carrier: | 52–90% | (Xylene, DMF, Methyl naphthalene, Cyclohexanone, Dichlorobenzene, Isophorone) |
| surface active agent: | 5–20% | (Sorpol 2680, Sorpol 3005X, Sorpol 3346) |
| others: | 0–20% | (Piperonyl butoxide: 0–20% Benzotriazole: 0–5%) |

(2) Oil solutions

| Active ingredient: | 5–30% | |
|---|---|---|
| liquid carrier: | 70–95% | (Xylene, Methyl cellosolve, Kerosene) |

(3) Flowables

| Active ingredient: | 5–70% | |
|---|---|---|
| liquid carrier: | 12.4–78.4% (water) | |
| surface active agent: | 1–10.5% | (Lunox 1000C, Sorpol 3353, Soprophor FL, Nippol, Agrisol S-710, Lignin sulfonic acid soda) |
| others: | 0–10% | Formalin 0–0.3%, Ethylene glycol 0–10%, Propylene glycol 0–10%) |

(4) Wettable powders (W.P.)

| Active ingredient: | 5–70% | |
|---|---|---|
| Solid carrier: | 15–89% | (Calcium carbonate, Kaolinite, Zeeklite D, Zeeklite PFP, Diatomaceous earth, Talc) |
| surface active agent: | 3–10% | (Sorpol 5039, Lunox 1000C, Sulfonic acid calcium, Sodium dodecyl-sulfonate, Sorpol 5050, Sorpol 005D, Sorpol 5029-0) |

(5) Dusts

| Active ingredient: | 0.01–30% | |
|---|---|---|
| solid carrier: | 67–99% | (Calcium carbonate, Kaolinite, Zeeklite, Talc) |
| others: | 0–3% | (Diisopropylphosphate 0–1.5%, Carplex #80: 0–3%) |

(6) Granules

| Active ingredient: | 0.1–30% | |
|---|---|---|
| solid carrier: | 67–99% | (Calcium carbonate, Kaolinite, Talc, Bentonite) |
| others: | 0–8% | (Calcium lignin sulfonate: 0–3 wt %, Polyvinylalcohol: 0–5%) |

2. Formulation Examples

Formulation Example 1: Emulsifiable concentrates

| Active ingredient | 20 parts |
|---|---|
| Xylene | 55 parts |
| N,N—dimethylformamide | 20 parts |
| Solpol 2680 (trade name, a mixture of a non-ionic surface-active agent and an anionic surface-active agent manufactured by Toho Chemicals, Co., Ltd., Japan) | 5 parts |

The above components are mixed intimately together to form an emulsifiable concentrate. Upon use, the emulsifiable concentrate is diluted with water up to one fiftieth to one twenty thousandth in concentration and applied at a rate of 0.005 to 50 kg of the active ingredient per hectare.

Formulation Example 2: Wettable powders

| Active ingredient | 25 parts |
|---|---|
| Zeeklite PFP (trade name, a mixture of kaolinite and sericite manufactured by Zeeklite Mining Industries Co., Ltd.) | 66 parts |
| Solpol 5039 (trade name, an anioic surface-active agent manufactured by Toho Chemical Co., Ltd., Japan) | 4 parts |
| Carplex #80 (trade name, white carbon manufactured by Shionogi Seiyaku K.K., Japan) | 3 parts |
| Calcium lingin sulfonate | 2 parts |

The above components are homogeneously mixed together and ground to form a wettable powder. Upon use, the wettable powder is diluted with water up to one fiftieth to one twenty thousandth and applied at a rate of 0.005 to 50 kg of the active ingredient per hectare.

Formulation Example 3: Oil solutions

| Active ingredient | 10 parts |
|---|---|
| methylcellosolve | 90 parts |

The above components are homogeneously mixed together to form an oil solution. Upon use, the oil solution is applied at a rate of 0.005 to 50 kg of the active ingredient per hectare.

Formulation Example 4: Dusts

| Active ingredient | 3.0 parts |
|---|---|
| Carplex #80 (trade name, white carbon manufactured by Shionogi Seiyaku K.K., Japan) | 0.5 parts |
| Clay | 95.0 parts |
| di-isopropyl phosphate | 1.5 parts |

The above components are homogeneously mixed together and ground to form a dust. Upon use, the dust is applied at a rate of 0.005 to 50 kg of the active ingredient per hectare.

Formulation Example 5: Granules

| Active ingredient | 5 parts |
|---|---|
| Bentonite | 54 parts |
| Talc | 40 parts |
| Calcium lignin sulfonate | 1 part |

The above components are mixed intimately together and ground, incorporated with a small amount of water and mixed together with stirring. The resulting mixture is granulated by means of extrusion-granulator and dried to form granules. Upon use, the granule is applied at a rate of 0.005 to 50 kg of the active ingredient per hectare.

Formulation Example 6: Flowables

| Active ingredient | 25 parts |
|---|---|
| Solpol 3353 (trade name, a nonionic surface-active agent manufactured by Toho Chemical Co., Ltd., Japan) | 10 parts |
| Runox 1000C (trade name, an anionic surface-active agent manufactured by Toho Chemical Co., Ltd., Japan) | 0.5 parts |
| 1% aqueous solution of Xanthan gum (natural high-molecular compound) | 20 parts |
| Water | 44.5 parts |

The above components except the active ingredient are homogeneously mixed together to form a solution, and thereto is added the active ingredient. The resulting mixture is throughly stirred, and wet-ground by means of sand mill to form a flowable. Upon use, the flowable is diluted up to one fiftieth to one twenty thousandth with water and applied at a rate of 0.005 to 50 kg of the active ingredient per hectare.

The compounds according to the present invention not only exhibit superior insecticidal action on hemiptera insect such as green rice leafhopper (*Nephotettix cincticeps*), lepidoptera insect such as diamondback moth (*Plutella xylostella*), Coleoptera and sanitary insect pests such as pale house mosquito (*Culex pipiens*), but are also useful for expelling mites parasitic on fruits and vegetables, such as two-spotted spider mite (*Tetranychus urticae*), Kanzawa spider mite (*Tetranychus kanzawai*), Carmine mite (*Tetranychus cinnabarinus*), citrus red mite (*Panonychus citri*) and European red mite (*Panonychus ulmi*), as well as ticks parasitic on animals, such as southern cattle tick (*Boophilus microplus*), cattle tick (*Boophilus annulatus*), gulf coast tick (*Amblyomma maculatum*), brown-ear tick (*Rhipicephalus appendiculaturs*) and *Haemaphysalis longicornis*. The main features of the compounds of the present invention reside in that the compounds are useful for the prevention or control of blight (or disease) of fruits and vegetables, such as powdery mildew, downy mildew, rust, rice blast disease (or rice blight) etc. in addition to having the above mentioned insecticidal, acaricidal and nematicidal actions. Accordingly, the compounds of the present invention are an excellent agricultural drug which enables control of pests and blight (or disease) simultaneously. Moreover, they are excellent as an expellent for ticks parasitic on animals such as domestic animals (e.g. cattle, horse, sheep and pig), domestic fowls, and other animals such as dog, cat, rabbit and the like.

The present invention is further explained in detail by way of the following test example.

TEST EXAMPLE 1

Insecticidal test on Green rice leafhopper (*Nephotettix cincticeps*)

20% emulsifiable concentrate of each of the present compounds described in the specification (some of which were applied with 25% wettable powder) was diluted with water containing an extender to prepare a 1000 ppm aqueous emulsion. This aqueous emulsion was dispersed in full amount to stems and leaves of paddy planted in a pot of 1/20000 and air-dried. Twenty second instar green rice leafhopper larvae which would show resistance to organic phosphorus type insecticides or carbamate type insecticides, per pot, were released in the pots. The paddies were covered with a cylindrical wire gauge and then placed in a thermostatic chamber. The numbers of the larvae killed was determined after 96 hours and the mortality thereof was calculated according to the equation below. Incidentally, the test was repeated twice for each compound.

$$\text{Mortality (\%)} = \frac{\text{number of the insect killed}}{\text{number of the insect released}} \times 100$$

As the results, the following compounds exhibited 100% of mortality.

| Compound Nos. | 14, 16, 17, 21, 22, 24, 25, 26, 29, 30, 31, 32, 33, 36, 38, 40, 41, 44, 45, 49, 53, 56, 61, 71, 72, 73, 75, 76, 77, 78, 79, 80, 82, 83, 84, 85, 87, 88, 89, 90, 92, 93, 97, 98, 99, 111, 112, 113, 127, 128, 129, 131, 148, 150, 174, 191, 202, 217, 220, 221, 226, 232, 235, 236, 239, 240, 267, 268, 269, 273, 277, 279, 280, 283, 284, 285, 288, 292, 323, 324, 359, 360, 364, 398, 426, 427, 429, 430, 432, 438, 443, 465, 466, 467, 468, 470, 472, 474, 475, 476, 477, 481, 482, 484, 488, 489, 490, 492, 494, 496, 498, 500, 514, 517, 518, 519, 520, 522, 524, 527, 528, 529, 540, 542, 565, 606, 609, 610, 643, 647, 652, 656, 657, 661, 664, 668, 670, 672, 676, 680, 702, 704, 708, 720, 722, 850, 851, 852, 857, 895, 1000, 1001, 1002 and 1143. |
|---|---|

TEST EXAMPLE 2

Insecticidal test on 28-spotted Lady beetle (*Henosepilachna vigintioctopunctata*)

A leaf of tomato was immersed for about 10 seconds in a 1000 ppm aqueous emulsion which had been prepared by diluting a 20% emulsifiable concentrate containing each compound described in the present specification (some of which were applied with 25% wettable powder) with water containing an extender and then air-drying. The leaf thus treated was placed in a laboratory dish, into which 10 second inster 28-spotted lady beetle larvae were released. The dish was then fitted with a cap provided with pores and then placed in a thermostatic chamber kept at 25° C. The number of the larvae killed was determined after 96 hours and the mortality thereof was calculated according to the equation described in the Test Example 1. Incidentally, the test was repeated twice for each compound.

As the results, the following compounds exhibited 100% mortality.

| Compound Nos. | 13, 14, 16, 17, 18, 21, 24, 25, 26, 29, 30, 31, 32, 33, 34, 36, 38, 40, 41, 44, |
|---|---|

-continued

| Compound Nos. | 45, 46, 49, 53, 55, 56, 70, 71, 72, 73, 74, 75, 76, 77, 78, 79, 80, 82, 83, 84, 85, 87, 88, 89, 90, 92, 93, 94, 95, 97, 99, 100, 111, 112, 113, 127, 128, 129, 131, 134, 150, 161, 174, 191, 192, 193, 194, 202, 216, 217, 218, 220, 221, 226, 232, 235, 236, 248, 250, 251, 268, 269, 279, 280, 283, 284, 285, 288, 290, 323, 324, 360, 426, 427, 429, 430, 432, 438, 443, 463, 465, 466, 467, 468, 470, 472, 474, 475, 476, 477, 480, 481, 482, 484, 488, 489, 490, 492, 494, 496, 498, 500, 514, 517, 518, 519, 520, 522, 524, 527, 528, 529, 540, 542, 609, 618, 643, 652, 657, 662, 664, 668, 702, 704, 722, 843, 850, 851, 852, 857, 863, 895, 1002, 1141 and 1143. |
|---|---|

TEST EXAMPLE 3

Acaricidal test on Kanzawa Spider Mite (*T. kanzawai*)

A leaf of kidney bean was cut into a round piece of 1.5 cm in diameter by a leaf punch, and then placed on a moistened filter paper on a polystyrol cup of 7 cm in a diameter. Each piece of the leaf was inoculated with 10 Kanzawa Spider Mite nymphs. Half a day after the inoculation, each 2 ml of an aqueous emulsion containing 1000 ppm of the present compuond described in the speciication (some of which were applied with 25% wettable powder) diluted with water containing an extender was applied to each polystyrol cup by means of a rotary spray tower. After 96 hours, the mortality of the nymph was determined according to the equation described in the Test Example 1. Incidentally, the test was repeated twice for each compound.

As the results, the following compounds exhibited 100% mortality.

| Compound Nos. | 13, 14, 15, 16, 17, 18, 24, 25, 26, 28, 29, 30, 31, 32, 33, 36, 40, 41, 44, 45, 49, 53, 55, 56, 70, 74, 76, 77, 78, 80, 83, 84, 85, 87, 88, 89, 90, 92, 93, 95, 97, 98, 99, 100, 111, 112, 113, 120, 129, 148, 150, 152, 161, 174, 191, 193, 194, 195, 197, 220, 221, 224, 226, 232, 235, 236, 240, 241, 250, 283, 287, 288, 290, 324, 344, 359, 360, 364, 398, 410, 421, 426, 427, 429, 430, 432, 438, 443, 463, 466, 467, 468, 470, 472, 475, 476, 477, 480, 481, 482, 488, 489, 490, 494, 514, 517, 518, 519, 520, 527, 529, 542, 606, 609, 610, 612, 643, 702, 704, 708, 720, 850, 851, 852, 857, 863, 895, 1001, 1002 and 1142. |
|---|---|

TEST EXAMPLE 4

Nematicidal test on Root-knot Nematode (*Meloidogyne sp.*)

Soil contaminated with root-knot nematode was placed in a polystyrol cup 8 cm in diameter. A liquid containing 1000 ppm of an active ingredient was prepared by diluting 20% emulsifiable concentrate containing a compound of the present invention (some of which were applied with 25% wettable powder) with water containing an extender. The soil contaminated with nematode and placed in the polystyrol cup was drenched with each 50 ml of the resulting liquid. After 48 hours, a tomato seedling as an indicator was transplanted into the soil thus treated. Thirty days after the transplanation, the roots of the tomato were washed with water and the root-knot parasitism was checked by observation. Incidentally, the test was repeated twice for each compound. As a result, no root-knot parasitism was observed in the roots of the tomato treated with the exhibit a strong nematicidal activity:

| Compound Nos. | 17, 72, 73, 76, 78, 84, 85, 90, 92, 93, 221, 268, 269, 280, 283, 359, and 465. |
|---|---|

TEST EXAMPLE 5

Insecticidal test on Green rice leafhopper (*Nephotettix cincticeps*)(Comparative test)

Test was conducted in accordance with Test Example 1 except that the concentration of each of the present compound and a control compound was changed to 500 ppm. The results are shown in Table 5. From the results, it can be seen that the present compounds exhibit much higher insecticidal activity than the known control compounds.

TEST EXAMPLE 6

Insectical test on 28-spotted Lady Beetle (*Henosepilachna vigintioctopunctata*)(Comparative test)

Test was conducted in accordance with Test Example 2 except that the concentration of each of the present compound and a control compound was changed to 500 ppm. The results are shown in Table 5. From the results, it can be seen that the present compunds exhibit much higher insecticidal activity then the known control compounds.

TEST EXAMPLE 7

Acaricidal test on Kanzawa Spider Mite (*T. kanzawai*)(Comparative test)

Test was conducted in accordance with Test Example 3 except that the concentration of each of the present compound and a control compound was changed to 500 ppm. The results are shown in Table 5. From the results, it can be seen that the present compounds exhibit much higher acaricidal activity than the known control compounds.

TABLE 5

| | Insecticidal Test (Comparative test) | | |
|---|---|---|---|
| Compound No. | Green rice leafhopper (mortality %) | 28-spotted lady beetle (mortality %) | Kanzawa spider mite (mortality %) |
| Present compound No. 40 | 100 | 100 | 100 |
| Present compound No. 92 | 100 | 100 | 100 |
| Present compound No. 465 | 100 | 100 | 100 |
| Control compound A | 0 | 20 | 0 |
| Control compound B | 20 | 0 | 50 |

The structural formulae of the present compounds in Table 5 are as follows:

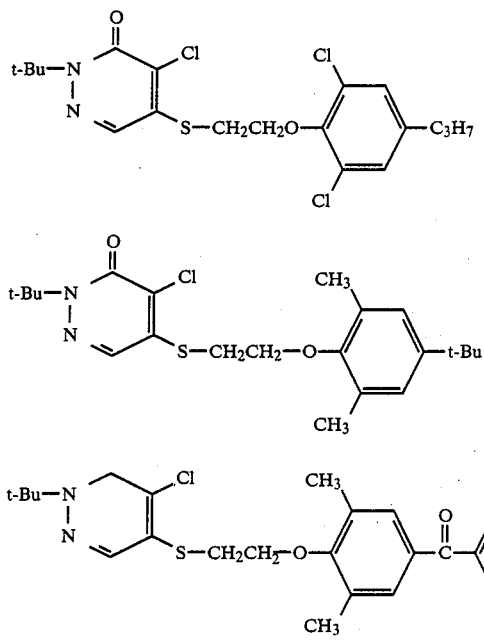

No. 40

No. 92

No. 465

On the other hand, the structural formulae of the control compounds are as follows:

Compound A

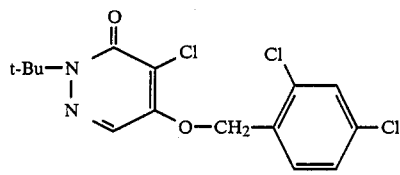

(compounds described in EP-A-0088384)

Compound B

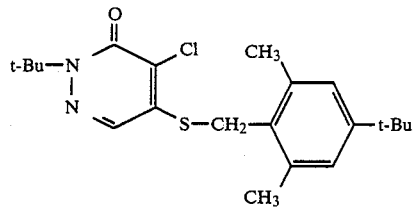

(compounds described in EP-A-0134439)
(Note that the above-mentioned "t-Bu" represents tertiary butyl group.)

TEST EXAMPLE 8

Residual activity text on 28-spotted lady beetle
(*Henosepilachna vigintioctopunctata*)

Tomato planted in a pot of 1/5000 are was sprayed well with a 500 ppm aqueous emulsion which had been prepared by diluting with water containing an extender 20% emulsifiable concentrate containing each compound described in the present specification (some of which were applied with 25% wettable powder), air-dried and kept in a greenhouse. After 10 days, leaf of the tomato thus treated was cut out and placed in a laboratory dish, into which 10 second inster 28-spotted lady beetle larvae were released. The dish was then fitted with a cap provided with pores and then placed in a thermostatic chamber kept at 25° C. The number of the larvae killed was checked after 96 hours and the mortality thereof was calculated according to the equation described in the Test Example 1. Incidentally, the test was repeated twice for each compound.

The following compounds exhibited 100% mortality.

| Compound Nos. | 22, 84, 85, 89, 90, 112, 113, 426, 427, 429, 430, 432, 438, 443, 465, 468, 470, 472, 481, 490, 496, 517, 520, 522, 528, 857 and 895. |

What is claimed is:
1. A compound of the following formula:

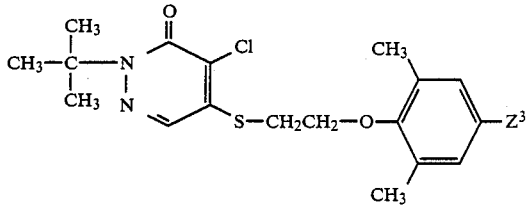

wherein $Z^3$ represents halogen atom, straight or branched chain alkyl group having 1 to 10 carbon atoms, alkoxy group having 1 to 10 carbon atoms, alkylcarbonyl having 2 to 10 carbon atoms, alkoxyalkyl group having 2 to 4 carbon atoms,

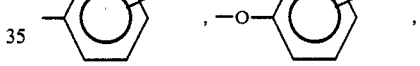

W represents halogen atom, alkyl group having 1 to 4 carbon atoms, alkoxy group having 1 to 4 carbon atoms, haloalkyl group having 1 to 4 carbon atoms, or nitro group, m is 0 or an integer of 1 to 2, and when m is 2, W may be same or different.

2. A composition for controlling insects, acari and nemati for agrricultural and horticultural use and containing as active ingredient a compound of the following formula:

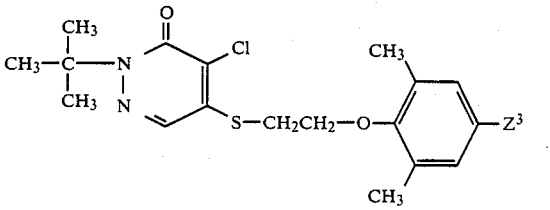

wherein $Z^3$ represents halogen atom, straight or branched chain alkyl group having 1 to 10 carbon atoms, alkoxy group having 1 to 10 carbon atoms, alkylcarbonyl having 2 to 10 carbon atoms, alkoxyalkyl group having 2 to 4 carbon atoms,

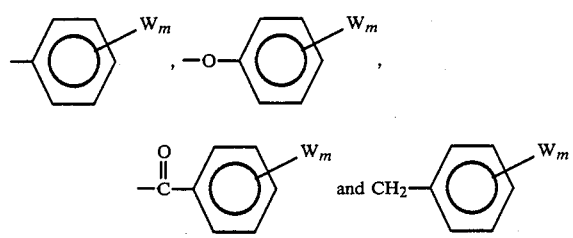

W represents halogen atom, alkyl group having 1 to 4 carbon atoms, alkoxy group having 1 to 4 carbon atoms, haloalkyl group having 1 to 4 carbon atoms, or nitro group, m is 0 or an integer of 1 to 2, and when m is 2, W may be same or different.

3. A 2-t-butyl-4-chloro-5-[2-2,6-dimethyl-4-(4-methylphenoxy)phenoxy ethylthio]-3(2H)-pyridazinone of claim 1 having the formula:

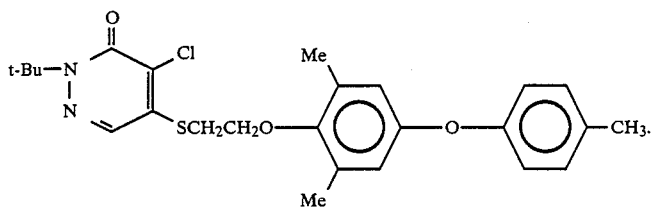

4. A 2-t-butyl-4-chloro-5-[2-(2,6-dimethyl-4-phenoxyphenoxy)ethylthio]-3(2H)-pyridazinone of claim 1 having the formula:

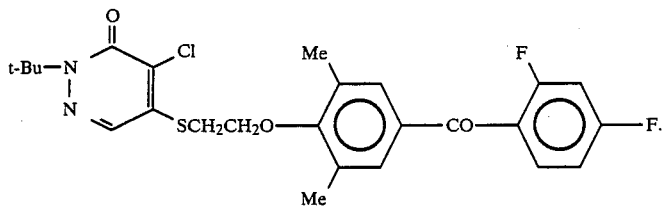

5. A 2-t-butyl-4-chloro-5-[2-{2,6-dimethyl-4-(2,4-difluorobenzoyl)phenoxy}ethylthio]-3(2H)-pyridazinone of claim 1 having the formula:

6. A 2-t-butyl-4-chloro-5-[2-(2,6-dimethyl-4-ethoxyphenoxy)ethylthio]-3(2H)-pyridazinone of claim 1 having the formula:

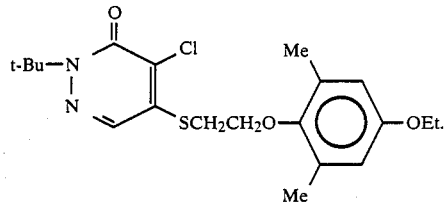

7. A 2-t-butyl-4-chloro-5-[2-(2,6-dimethyl-4-methoxymethyl-phenoxy)ethylthio]-3(2H)-pyridazinone of claim 1 having the formula:

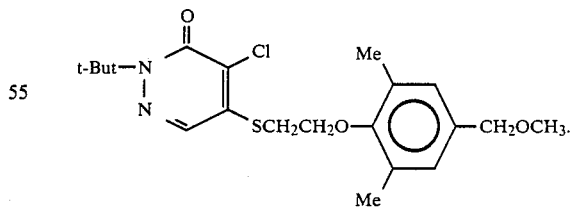

* * * * *